(12) United States Patent
Hulliger

(10) Patent No.: US 9,339,316 B2
(45) Date of Patent: May 17, 2016

(54) DYNAMIC BONE FIXATION ELEMENT

(71) Applicant: DePuy Synthes Products, Inc., Raynham, MA (US)

(72) Inventor: Urs Hulliger, Oberdorf (CH)

(73) Assignee: DePuy Synthes Products, Inc., Raynham, MA (US)

(*) Notice: Subject to any disclaimer, the term of this patent is extended or adjusted under 35 U.S.C. 154(b) by 258 days.

(21) Appl. No.: 13/788,531

(22) Filed: Mar. 7, 2013

(65) Prior Publication Data

US 2013/0245697 A1    Sep. 19, 2013

Related U.S. Application Data

(60) Provisional application No. 61/619,072, filed on Apr. 2, 2012, provisional application No. 61/609,992, filed on Mar. 13, 2012.

(51) Int. Cl.
*A61B 17/86* (2006.01)
*A61B 17/80* (2006.01)
(Continued)

(52) U.S. Cl.
CPC ............. *A61B 17/8685* (2013.01); *A61B 17/80* (2013.01); *A61B 17/84* (2013.01); *A61B 17/88* (2013.01); *A61B 17/686* (2013.01)

(58) Field of Classification Search
CPC ...... A61B 17/68; A61B 17/686; A61B 17/80; A61B 17/8052; A61B 17/8057; A61B 17/84; A61B 17/844; A61B 17/86; A61B 17/8605; A61B 17/8625; F16B 35/041
USPC .......................... 606/300–321; 411/383, 424
See application file for complete search history.

(56) References Cited

U.S. PATENT DOCUMENTS 36,014 A     7/1862   Meissner
240,780 A    4/1881   Smith
(Continued)

FOREIGN PATENT DOCUMENTS

CA    2 560 898    10/2005
CH      379230      6/1964
(Continued)

OTHER PUBLICATIONS

Lauterburg et al., "Forces Involved in Lower Limb Lengthening: An In Vivo Biomechanical Study", Journal of Orthopaedic Research, Sep. 2006, 24(9), 1815-1822.
(Continued)

*Primary Examiner* — Christian Sevilla
*Assistant Examiner* — Eric S Gibson
(74) *Attorney, Agent, or Firm* — Baker & Hostetler LLP

(57) ABSTRACT

A dynamic bone fixation element can include a sleeve elongate along a first direction and a fixation member. The sleeve can define a channel that extends from a proximal end through to a distal end along the first direction. The channel has a first cross-sectional dimension. The fixation member has a head, a shaft extending from the head and elongate along a second direction, and an abutment member extending from the shaft and integral with the shaft, wherein the shaft extends through the channel such that the sleeve is captured between the abutment member and the head. At least a portion of the shaft that is within the channel has a second cross-sectional dimension that is less than the first cross-sectional dimension such that the fixation member is moveable with respect to the sleeve along a direction that has a directional component transverse to the first direction.

41 Claims, 16 Drawing Sheets

(51) Int. Cl.
*A61B 17/84* (2006.01)
*A61B 17/88* (2006.01)
*A61B 17/68* (2006.01)

(56) References Cited

U.S. PATENT DOCUMENTS

| | | | |
|---|---|---|---|
| 240,913 | A | 5/1881 | Lupton |
| 370,136 | A | 9/1887 | Goddu |
| 534,164 | A | 2/1895 | Larsh |
| 890,447 | A | 6/1908 | Perry |
| 1,231,643 | A | 7/1917 | Parnall |
| 1,462,126 | A | 7/1923 | Ross |
| 1,469,126 | A * | 9/1923 | Thomas ............ 411/338 |
| 1,756,973 | A | 5/1930 | Conner |
| 1,828,287 | A | 10/1931 | MacBean |
| 1,828,402 | A | 10/1931 | Geyer |
| 1,983,962 | A | 12/1934 | Barber et al. |
| 2,045,757 | A | 6/1936 | Constantin |
| 2,567,372 | A | 9/1951 | Gelpcke |
| 2,586,556 | A * | 2/1952 | Mullikin ............ 411/339 |
| 2,672,070 | A | 3/1954 | Forster |
| 2,888,853 | A | 6/1959 | Pachmayr |
| 3,077,809 | A | 2/1963 | Harding et al. |
| 3,298,273 | A * | 1/1967 | McKelvey ............ 411/1 |
| 3,350,811 | A | 11/1967 | Bender |
| 3,455,360 | A | 7/1969 | Simons |
| 3,466,966 | A | 9/1969 | Brown |
| 3,495,494 | A | 2/1970 | Scott |
| 3,942,329 | A | 3/1976 | Babcock |
| 3,945,070 | A | 3/1976 | Hauser |
| 4,269,248 | A | 5/1981 | MacLean et al. |
| 4,348,141 | A | 9/1982 | Dahl |
| 4,395,924 | A | 8/1983 | Callahan |
| 4,402,160 | A | 9/1983 | Brusasco |
| 4,432,683 | A | 2/1984 | Polos |
| 4,437,286 | A | 3/1984 | Maguire |
| 4,589,179 | A | 5/1986 | Hulting, Jr. |
| 4,724,628 | A | 2/1988 | Schreiner |
| 4,756,654 | A | 7/1988 | Clough |
| 4,854,797 | A | 8/1989 | Gourd |
| 4,870,957 | A * | 10/1989 | Goble et al. ............ 623/13.12 |
| 4,906,154 | A | 3/1990 | Sheppard |
| 4,947,502 | A | 8/1990 | Engelhardt |
| 4,959,064 | A | 9/1990 | Engelhardt |
| 4,974,986 | A | 12/1990 | Cook |
| 5,061,137 | A * | 10/1991 | Gourd ............ 411/510 |
| 5,074,865 | A | 12/1991 | Fahmy |
| 5,092,727 | A | 3/1992 | Moghe |
| 5,102,276 | A | 4/1992 | Gourd |
| 5,209,753 | A * | 5/1993 | Biedermann et al. ............ 606/304 |
| 5,351,806 | A | 10/1994 | Ohtsuji et al. |
| 5,501,541 | A | 3/1996 | Gomes |
| 5,569,251 | A * | 10/1996 | Baker et al. ............ 606/281 |
| 5,676,356 | A | 10/1997 | Ekonen et al. |
| 5,797,234 | A | 8/1998 | Theodorou |
| 6,083,224 | A | 7/2000 | Gertzbein et al. |
| 6,158,937 | A | 12/2000 | Okun |
| 6,368,326 | B1 | 4/2002 | Dakin et al. |
| 6,475,242 | B1 | 11/2002 | Bramlet |
| 6,508,841 | B2 | 1/2003 | Martin et al. |
| 6,524,316 | B1 * | 2/2003 | Nicholson et al. ............ 606/326 |
| 6,527,774 | B2 | 3/2003 | Lieberman |
| 6,551,320 | B2 | 4/2003 | Lieberman |
| 6,554,526 | B1 | 4/2003 | Egelandsdal |
| 6,592,292 | B1 | 7/2003 | Jansson |
| 6,626,911 | B1 * | 9/2003 | Engman et al. ............ 606/916 |
| 6,656,184 | B1 | 12/2003 | White et al. |
| 6,908,275 | B2 | 6/2005 | Nelson et al. |
| 6,955,513 | B2 | 10/2005 | Niku |
| 7,153,326 | B1 | 12/2006 | Metzger |
| 7,175,626 | B2 | 2/2007 | Neff |
| 7,249,923 | B2 | 7/2007 | Niku |
| 8,114,141 | B2 | 2/2012 | Appenzeller et al. |
| 8,388,660 | B1 * | 3/2013 | Abdou ............ 606/267 |
| 2002/0007508 | A1 | 1/2002 | Grepper et al. |
| 2002/0150444 | A1 * | 10/2002 | Mhaimeed ............ 411/383 |
| 2002/0198527 | A1 | 12/2002 | Muckter |
| 2003/0133769 | A1 * | 7/2003 | Schultz ............ 411/403 |
| 2003/0180117 | A1 | 9/2003 | Niku |
| 2003/0202861 | A1 * | 10/2003 | Nelson et al. ............ 411/487 |
| 2004/0202526 | A1 | 10/2004 | Bunch, Jr. |
| 2005/0008449 | A1 * | 1/2005 | Horita ............ 411/383 |
| 2005/0010215 | A1 | 1/2005 | Delecrin et al. |
| 2005/0021036 | A1 * | 1/2005 | Whitmore et al. ............ 606/73 |
| 2005/0143823 | A1 | 6/2005 | Boyd et al. |
| 2005/0154390 | A1 | 7/2005 | Biedermann et al. |
| 2005/0177167 | A1 | 8/2005 | Muckter |
| 2005/0222575 | A1 * | 10/2005 | Ciccone et al. ............ 606/104 |
| 2005/0277940 | A1 * | 12/2005 | Neff ............ 606/73 |
| 2006/0074421 | A1 * | 4/2006 | Bickley et al. ............ 606/72 |
| 2006/0195099 | A1 | 8/2006 | Bottlang |
| 2006/0229615 | A1 | 10/2006 | Abdou |
| 2006/0247642 | A1 * | 11/2006 | Stone et al. ............ 606/73 |
| 2006/0264954 | A1 * | 11/2006 | Sweeney et al. ............ 606/73 |
| 2007/0038219 | A1 * | 2/2007 | Matthis et al. ............ 606/72 |
| 2007/0167948 | A1 | 7/2007 | Abdou |
| 2007/0191958 | A1 | 8/2007 | Abdou |
| 2007/0233062 | A1 | 10/2007 | Berry |
| 2007/0282342 | A1 | 12/2007 | Niederberger et al. |
| 2008/0021465 | A1 * | 1/2008 | Shadduck et al. ............ 606/61 |
| 2008/0071273 | A1 | 3/2008 | Hawkes et al. |
| 2008/0188899 | A1 | 8/2008 | Bottlang et al. |
| 2009/0018587 | A1 | 1/2009 | Bottlang |
| 2009/0099610 | A1 * | 4/2009 | Johnson et al. ............ 606/86 R |
| 2009/0157123 | A1 * | 6/2009 | Appenzeller et al. ............ 606/301 |
| 2009/0248089 | A1 * | 10/2009 | Jacofsky et al. ............ 606/311 |
| 2010/0268285 | A1 * | 10/2010 | Tipirneni et al. ............ 606/309 |
| 2010/0331881 | A1 * | 12/2010 | Hart ............ 606/232 |
| 2011/0046682 | A1 * | 2/2011 | Stephan et al. ............ 606/305 |
| 2011/0106166 | A1 | 5/2011 | Keyer et al. |
| 2011/0202096 | A1 * | 8/2011 | White et al. ............ 606/86 R |
| 2011/0319946 | A1 * | 12/2011 | Levy et al. ............ 606/309 |
| 2012/0034046 | A1 * | 2/2012 | Cooper et al. ............ 411/361 |
| 2012/0078369 | A1 * | 3/2012 | Hart ............ 623/13.14 |
| 2012/0089175 | A1 * | 4/2012 | LeCronier et al. ............ 606/205 |
| 2012/0172934 | A1 * | 7/2012 | Fisher et al. ............ 606/304 |
| 2013/0226251 | A1 * | 8/2013 | Chegini et al. ............ 606/325 |
| 2013/0245697 | A1 * | 9/2013 | Hulliger ............ 606/281 |
| 2014/0005731 | A1 * | 1/2014 | Biedermann et al. ............ 606/328 |
| 2014/0142639 | A1 * | 5/2014 | Vennard et al. ............ 606/291 |
| 2014/0172026 | A1 * | 6/2014 | Biedermann et al. ............ 606/326 |

FOREIGN PATENT DOCUMENTS

| | | |
|---|---|---|
| DE | 1872944 | 5/1963 |
| DE | 9300056 | 3/1993 |
| DE | 19741087 | 4/1999 |
| DE | 29915204 | 12/1999 |
| DE | 10107201 | 9/2002 |
| DE | 102004006746 | 5/2005 |
| EP | 0482875 | 4/1992 |
| EP | 0820731 | 1/1998 |
| EP | 1273269 | 1/2003 |
| FR | 736058 | 11/1932 |
| FR | 958192 | 3/1950 |
| FR | 2634371 | 1/1990 |
| FR | 2784019 | 4/2000 |
| FR | 2915082 | 10/2008 |
| GB | 572218 | 9/1945 |
| GB | 1051351 | 12/1966 |
| GB | 1067304 | 5/1967 |
| JP | 2003-010199 | 1/2003 |
| JP | 2006-528536 | 12/2006 |
| SU | 512315 | 9/1974 |
| SU | 838124 | 9/1979 |
| SU | 838125 | 9/1979 |
| WO | WO 95/02373 | 1/1995 |
| WO | WO 02/24087 | 3/2002 |
| WO | WO 2005/044117 | 5/2005 |
| WO | WO 2005/092226 | 10/2005 |
| WO | WO 2006/089292 | 8/2006 |
| WO | WO 2007/049097 | 5/2007 |
| WO | WO 2007/092869 | 8/2007 |
| WO | WO 2007/095333 | 8/2007 |

(56) References Cited

FOREIGN PATENT DOCUMENTS

| WO | WO 2007/115016 | 10/2007 |
| WO | WO 2008/034130 | 3/2008 |
| WO | WO 2008/097403 | 8/2008 |

OTHER PUBLICATIONS

Steen et al., "Limb Lengthening by Diaphyseal Corticotomy, Callus Distraction, and Dynamic Axial Fixation. An Experimental Study in the Ovine Femur", Journal of Orthopaedic Research, Sep. 1988, 6(5), 730-735.

International Patent Application No. PCT/US2008/086390: International Search Report and Written Opinion dated Jun. 18, 2009, 18 pages.

Bottlang et al., "Far Cortical Locking Can Reduce Stiffness of Locked Plating Constructs While Retaining Construct Strength", J. Bone Joint Surg. Am., Aug. 2009, 91(8), 1985-1994.

* cited by examiner

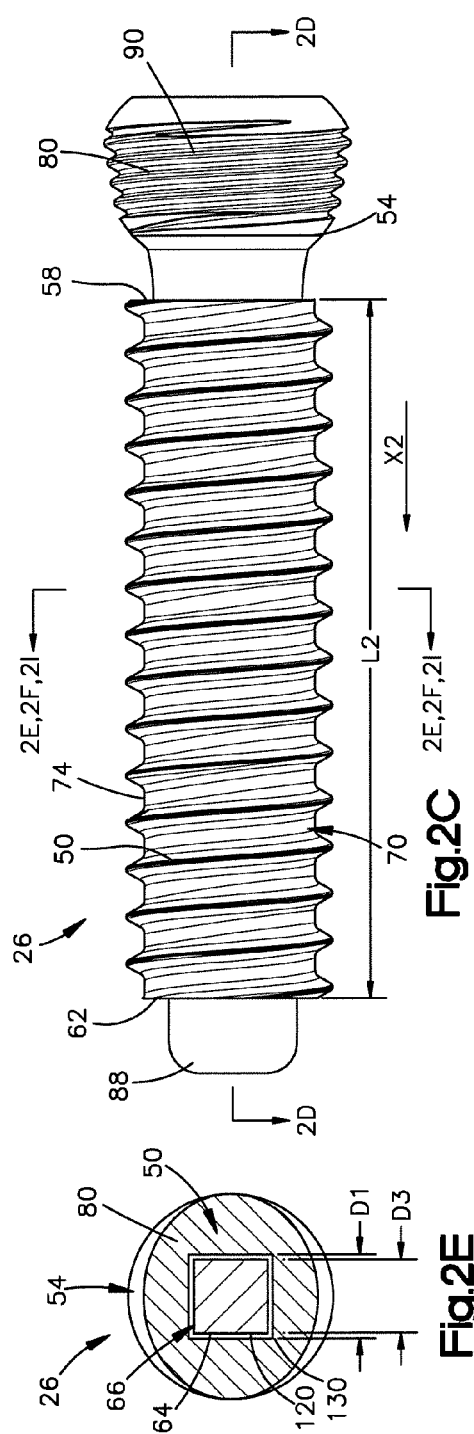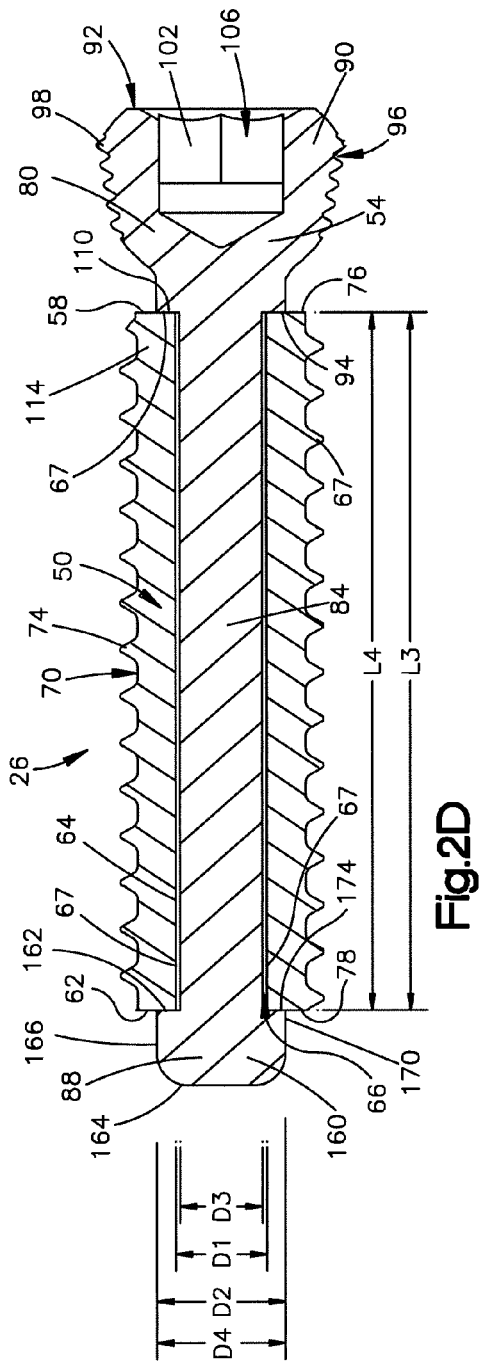
Fig.2C
Fig.2D
Fig.2E

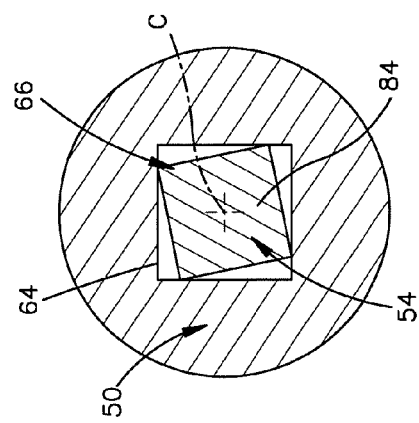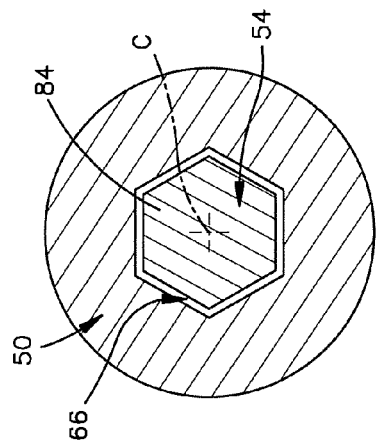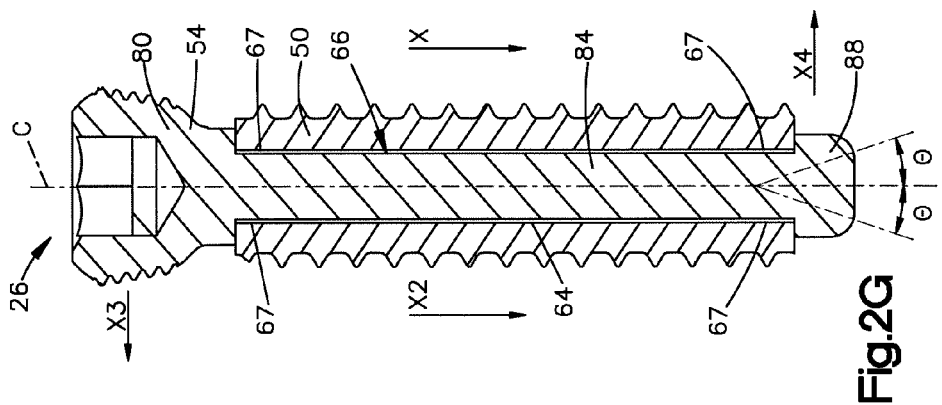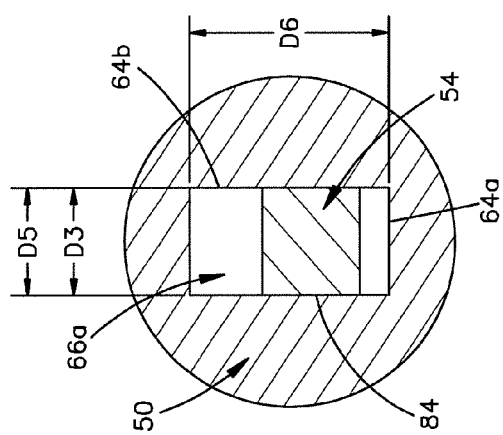

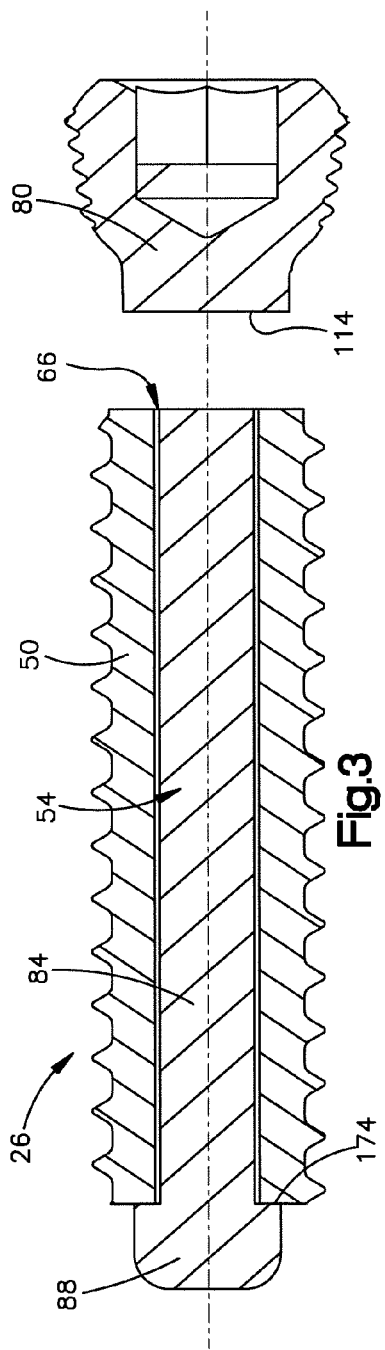
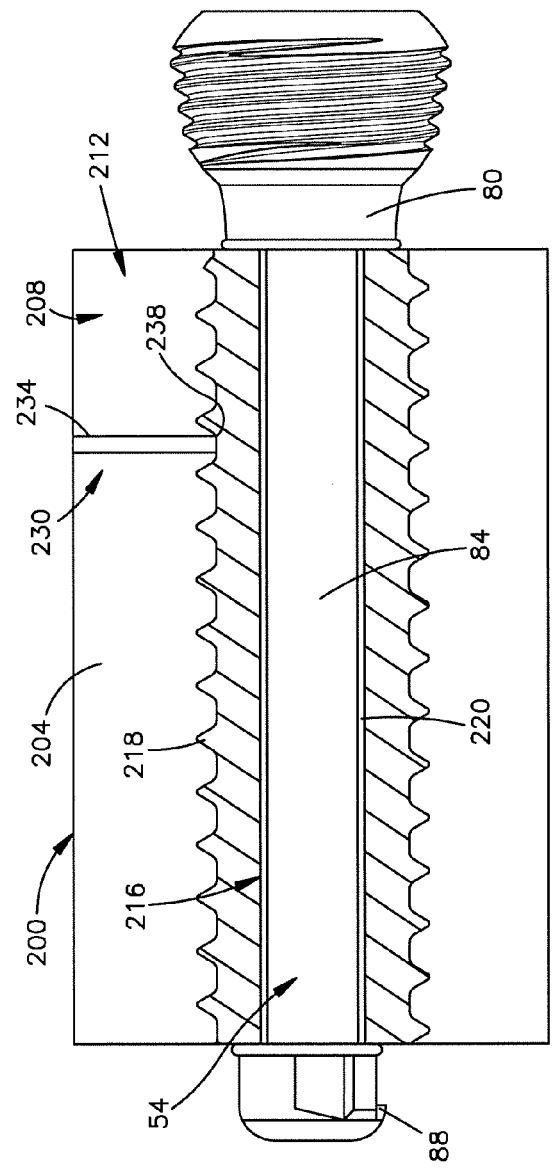
Fig.3
Fig.4

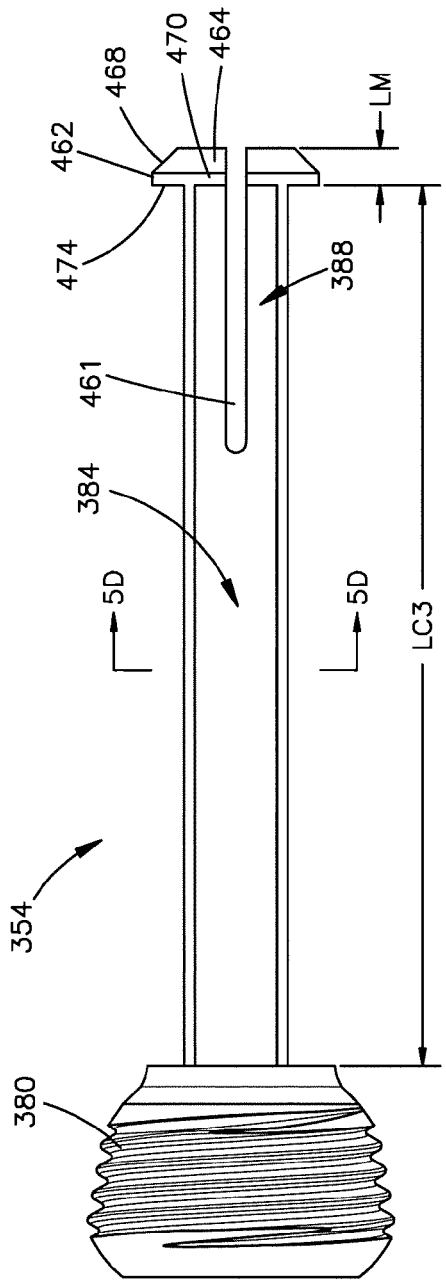
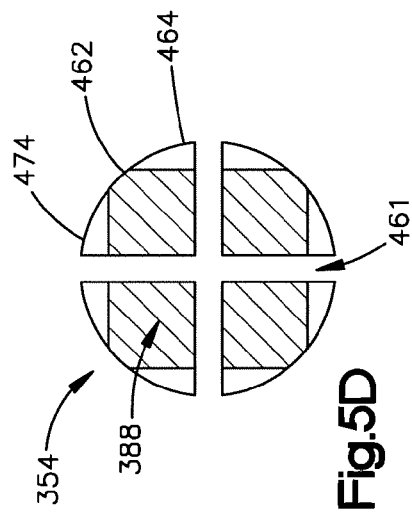

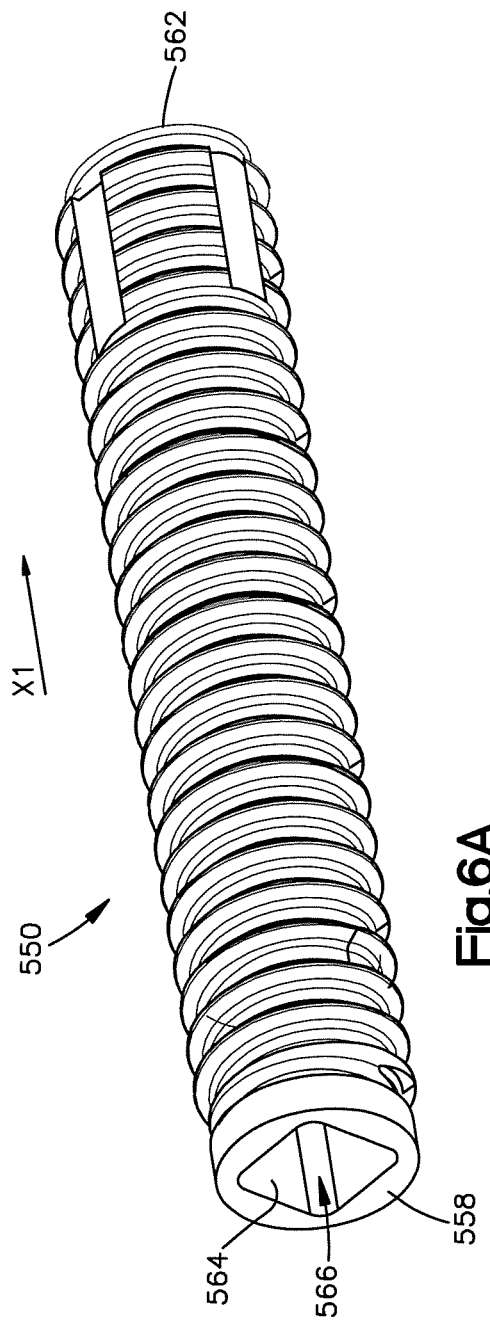
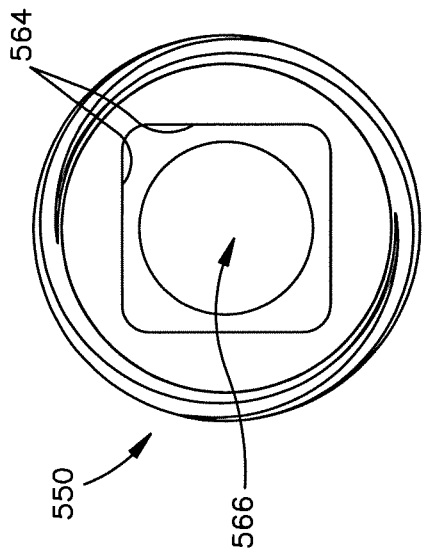
Fig.6A
Fig.6B

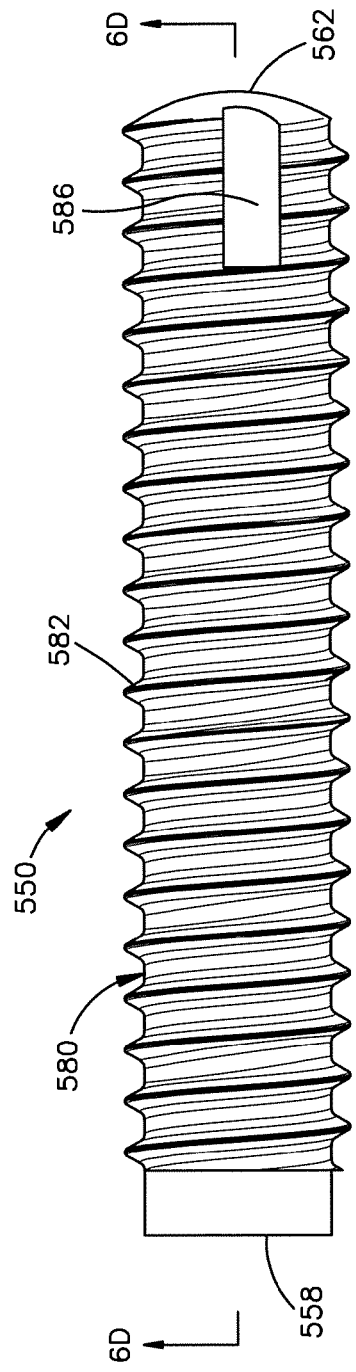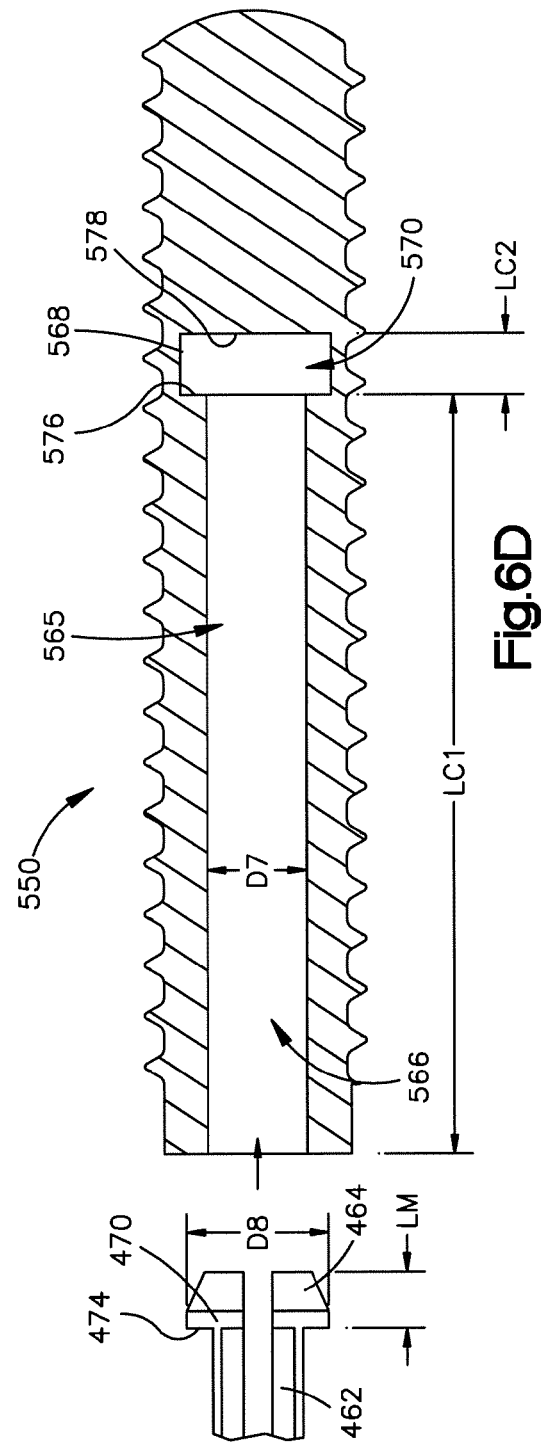
Fig.6C
Fig.6D

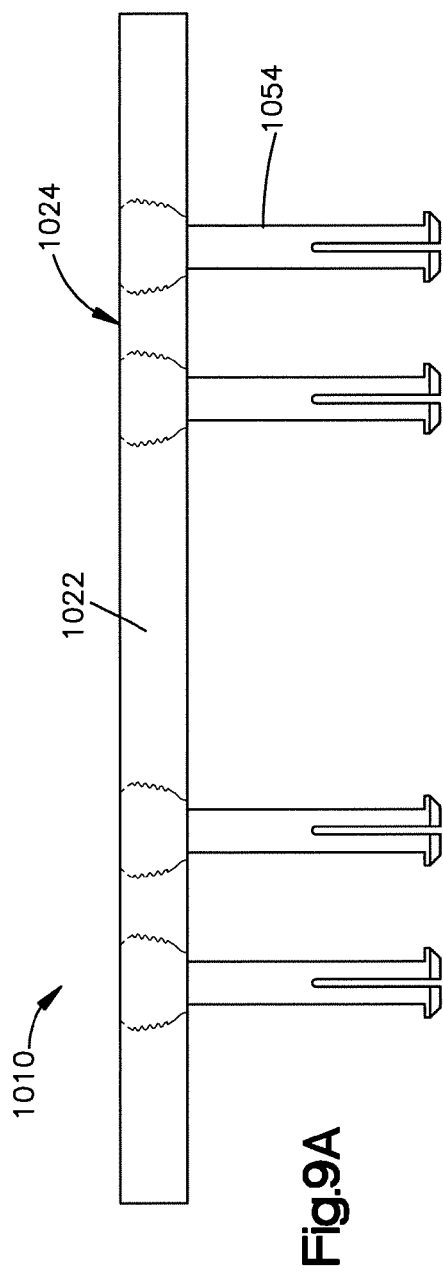
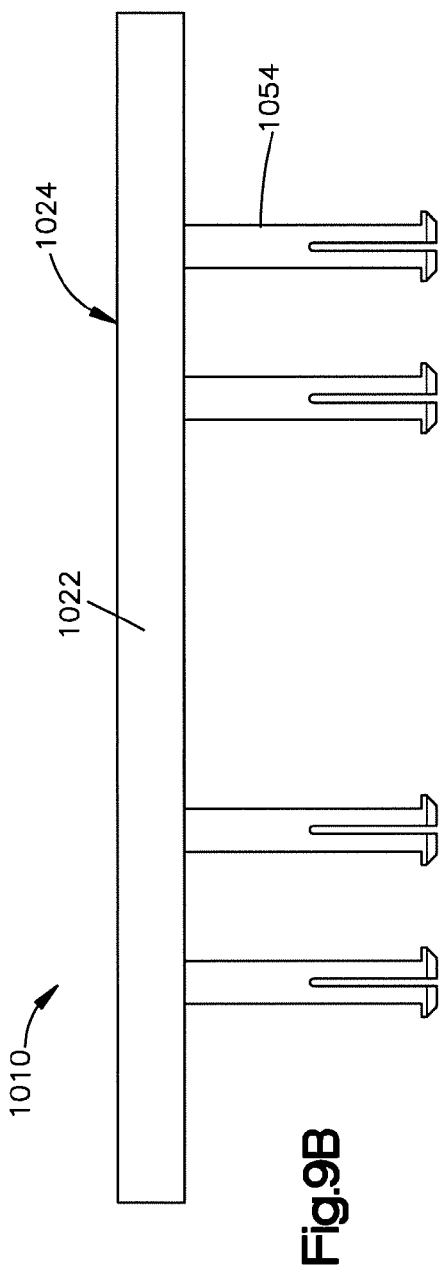

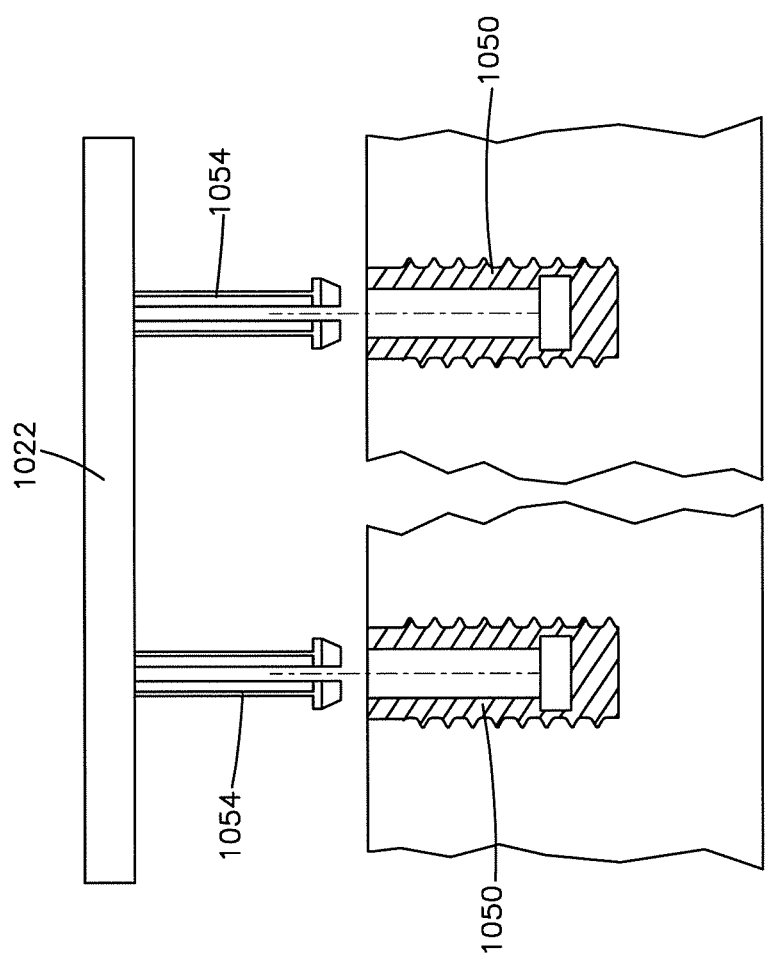

DYNAMIC BONE FIXATION ELEMENT

CROSS-REFERENCE TO RELATED APPLICATIONS

This application claims the benefit of U.S. Provisional Application No. 61/609,992 filed Mar. 13, 2012 and U.S. Provisional Application No. 61/619,072 filed Apr. 2, 2012 the contents of each of which are hereby incorporated by reference in their entirety herein.

BACKGROUND

Millions of people suffer from bone fractures each year. Treatment of this condition is frequently accomplished by rigid fixation which involves affixing a load carrier (e.g. a bone plate, a rod, etc.) to a patient's bone fragments via a plurality of bone fixation elements (e.g. bone screws, hooks, fixation members, rivets, etc.) in order to stabilize bone fragments relative to each other.

Dynamic fixation of the load carrier is believed to reduce the amount of stress generally associated with rigid fixation. In some cases the load carrier is affixed to the bone fragments using dynamic locking crews. Certain dynamic locking screws include a fixation member that is welded to a sleeve. The sleeves engage bone and the fixation member is movable about the weld and relative to the sleeve to thereby allow for micro-movement of the bone fragments relative to each other. Known dynamic locking screws may be costly to manufacture and may be difficult to manufacture for certain applications. Therefore, improved dynamic fixation elements may be desired.

SUMMARY

In one embodiment, a dynamic bone fixation element is configured to couple a load carrier to bone. The dynamic bone fixation element can include a sleeve that is elongate along a first direction. The sleeve can define a proximal end, a distal end spaced from the proximal end along the first direction, and a channel that extends from the proximal end and toward the distal end along the first direction. The channel can have a first cross-sectional dimension measured along a direction that is perpendicular to the first direction, and the sleeve can further define an outer surface that is configured to engage bone. The dynamic bone fixation element can further include a fixation member having a head, a shaft that extends from the head along a second direction, and an abutment member that extends from the shaft, wherein the shaft is configured to extend into the channel such that at least a portion of the sleeve is captured between the abutment member and the head to thereby couple the fixation member to the sleeve. At least a portion of the shaft that is configured to be within the channel has a second cross-sectional dimension along a direction perpendicular to the second direction, the second cross-sectional dimension being less than the first cross-sectional dimension such that the fixation member is moveable with respect to the sleeve along a direction that has a directional component transverse to the first direction.

In another embodiment, a dynamic bone fixation element can include a sleeve that is elongate along a first direction, and a fixation member coupled to the sleeve. The sleeve can define a proximal end, a distal end spaced from the proximal end along the first direction, and an inner surface that at least partially defines a channel. The channel can extend from the proximal end through to the distal end along the first direction. The sleeve further defines an outer surface that is configured to engage bone. The fixation member can have a head, a shaft extending from the head, and an abutment member extending from the shaft. The fixation member is movable with respect to the sleeve along the first direction, and both the abutment member and the head define respective abutment surfaces that are sized to contact the sleeve so as to limit translation of the fixation member relative to the sleeve along the first direction.

In another embodiment, a dynamic bone fixation element can include a sleeve that is elongate along a first direction, and a fixation member. The sleeve defines a proximal end, a distal end spaced from the proximal end along the first direction, and an inner surface that at least partially defines a channel. The channel extends from the proximal end through to the distal end along the first direction. The sleeve further defines an outer surface that is configured to engage bone. The fixation member can have a head, a shaft extending from the head and into the channel, and an abutment member extending from the shaft. The abutment member at least partially couples the fixation member to the sleeve such that both a proximal end and a distal end of the fixation member are moveable with respect to the sleeve along a direction that has a directional component perpendicular to the first direction.

Methods of making a dynamic fixation element are also disclosed. In one embodiment, a shaft of a fixation member is inserted through a channel of a sleeve along a longitudinal direction until a first abutment surface of the fixation member contacts a first end of the sleeve, the sleeve having an inner surface that at least partially defines the channel, and an outer surface that is configured to engage bone, the shaft has a surface that is spaced apart from the inner surface when the shaft is inserted into the channel such that the fixation member can move relative to the sleeve along a direction that is transverse to the longitudinal direction. A second abutment surface is then coupled to the fixation member such that the sleeve is captured between the first and second abutment surfaces.

Methods of fixing a load carrier across a bone gap defined between first and second bone portions is also disclosed. In one embodiment the method includes coupling a load carrier to a first bone portion with a first dynamic fixation element, the first dynamic fixation element having a first fixation member and a first sleeve that is captured between first and second abutment surfaces of the first fixation member, the first sleeve having an inner surface and the first fixation member including a shaft that has a first surface that is spaced apart from the inner surface of the first sleeve such that the first fixation member can move relative to the first sleeve. The method further includes coupling the load carrier to a second bone portion with a second dynamic fixation element, the second dynamic fixation element having a second fixation member and a second sleeve that is captured between first and second abutment surfaces of the second fixation member, the second sleeve having an second inner surface and the second fixation member including a shaft that has a second surface that is spaced apart from the second inner surface of the second sleeve such that the second fixation member can move relative to the second sleeve.

BRIEF DESCRIPTION OF THE DRAWINGS

The foregoing summary, as well as the following detailed description of embodiments of the application, will be better understood when read in conjunction with the appended drawings. For the purposes of illustrating the methods, fixation elements and systems of the present application, there is shown in the drawings preferred embodiments. It should be understood, however, that the application is not limited to the precise methods, fixation elements, and systems shown. In the drawings:

FIG. 2C is a side elevation view of the dynamic fixation element shown in FIG. 2A;

FIG. 2D is a cross-sectional view of the dynamic fixation element shown in FIG. 2C through the line 2D-2D;

FIG. 2E is a cross-sectional view of the dynamic fixation element shown in FIG. 2C through the line 2E-2E;

FIG. 2F is a cross-sectional view of the dynamic fixation element shown in FIG. 2C through the line 2F-2F showing a channel of the sleeve in accordance with another embodiment;

FIG. 2G is a cross-sectional view of the dynamic fixation element showing at least some of the directions in which the fixation member can move relative to the sleeve;

FIG. 2H is a cross-sectional view of the dynamic fixation element with the fixation member rotated counter clockwise relative to the sleeve;

FIG. 2I is a cross-sectional view of a dynamic fixation element shown in FIG. 2C through the line 2I-2I in accordance with another embodiment;

FIG. 3 is a cross-sectional view of the dynamic fixation element shown in FIG. 2D prior to the head of the fixation member being welded to the shaft of the fixation member to thereby couple the fixation member to the sleeve;

FIG. 4 is a side elevation view of a fixation member positioned in a mold, the mold being configured to receive a material to thereby form a sleeve between the head and the abutment member of the fixation member

FIG. 5C is a side elevation view of the fixation member shown in FIG. 5B;

FIG. 5D is a cross-sectional view of the fixation member shown in FIG. 5C through the line 5D-5D;

FIG. 6A is a perspective view of a sleeve in accordance with another embodiment that can be coupled to the fixation member shown in FIG. 5B;

FIG. 6B is a top plan view of the sleeve shown in FIG. 6A;

FIG. 6C is a side elevation view of the sleeve shown in FIG. 6A;

FIG. 6D is a cross-sectional view of the sleeve shown in FIG. 6C through the line 6D-6D;

FIG. 9A is a side elevation view of a bone plate and a plurality of fixation members that are pre-assembled so as to form a pre-made implant;

FIG. 9B is a side elevation view of a bone plate and a plurality of fixation members that are integrally formed with the bone plate so as to form a pre-made monolithic implant;

FIG. 9E is a side perspective view of an implant as shown in either FIG. 9A or 9B being coupled to sleeves that have been driven into respective anatomical structures.

DETAILED DESCRIPTION

Figure 1:
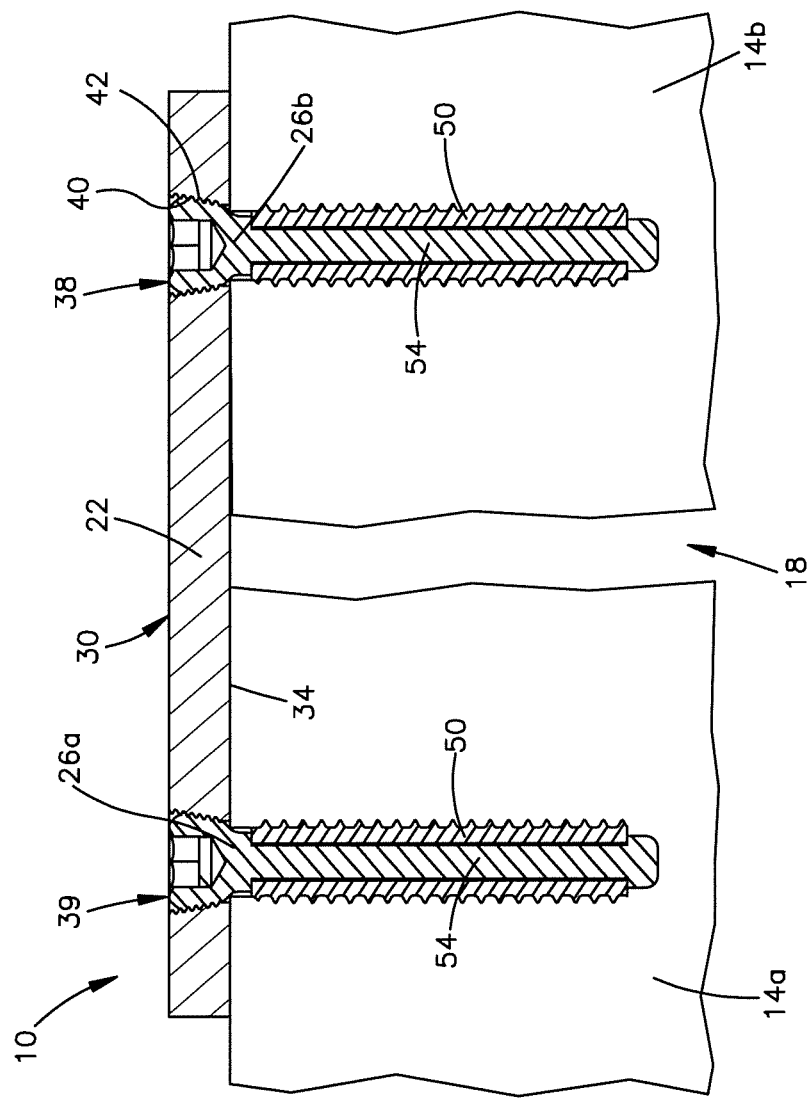
FIG. 1 is a side elevation view of a bone fixation system according to an embodiment, the fixation system having a load carrier and at least two dynamic fixation elements coupling the load carrier to respective anatomical structures that are separated by a gap, the dynamic fixation elements are shown in cross-section for clarity.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Referring to FIG. 1 a bone fixation system 10 is configured to affix a first substrate or anatomical body 14a and a second substrate or anatomical body 14b relative to teach other such that micro-movement of the first and second anatomical bodies 14a and 14b is permitted. The anatomical bodies 14a and 14b can each be configured as a bone fragment, soft tissue, implant, vertebral body, or any alternative structure configured to be attached to another anatomical body. In accordance with the illustrated embodiment, the first and second anatomical bodies 14a and 14b are configured as first and second bone fragments, separated by a bone gap, such as a fracture 18. It should be appreciated, however, that the gap defined between the first and second anatomical bodies can be defined by conditions other than fractures, including anatomical deformities and gaps defined between implants and bones or soft tissue or even a gap (i.e. intervertebral space) defined between adjacent vertebral bodies.

The bone fixation system 10 can include a load carrier 22, at least one dynamic bone fixation element 26, such as a first dynamic bone fixation element 26a that affixes the load carrier 22 to the first anatomical body 14a, and at least one bone fixation element 26 such as a second dynamic bone fixation element 26b that affixes the load carrier 22 to the second anatomical body 14b. The dynamic bone fixation elements 26 are configured to allow for micro-movement of the anatomical bodies 14a and 14b relative to each other.

With continued reference to FIG. 1, the load carrier 22 can be configured as a bone plate having an upper surface 30, a lower bone contacting surface 34, and at least two bone fixation holes 38 that extend from the upper surface 30 through to the lower bone contacting surface 34. The load carrier further includes respective inner surfaces 40 that define the fixation holes 38. Each respective inner surface 40 carries a thread 42 that is configured to engage the dynamic bone fixation elements 26. In the illustrated embodiment the thread 42 extends completely around each surface 40, though it should be appreciated that each thread 42 can extend partially around each surface 40 so as to define a plurality of segments of threads. While the load carrier 22 is illustrated as a bone plate, it should be appreciated that the load carrier 22 can be configured as a rod or other stabilizing structure as desired.

Now in reference to FIGS. 2A-2E, the dynamic bone fixation element 26 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the bone fixation system 10 is coupled to the spine, the transverse direction T extends vertically generally along the superior-inferior (or caudal-cranial) direction, while the plane defined by the longitudinal direction L and the lateral direction A lies generally in the anatomical plane defined by the anterior-posterior direction, and the medial-lateral direction, respectively. Accordingly, the directional terms "vertical" and "horizontal" are used to describe the dynamic bone fixation element 26 and its components as illustrated merely for the purposes of clarity and illustration.

As shown in FIGS. 1 and 2A-2E, each dynamic bone fixation element 26 is configured to affix the load carrier 22 to an anatomical structure such as bone. Each bone fixation element 26 includes a sleeve 50 and a fixation member 54 coupled to the sleeve 50. The fixation member 54 is coupled to the sleeve 50 such that the fixation member 54 is capable of moving relative to the sleeve 50 along at least one of the transverse direction, lateral direction, and longitudinal direction. The fixation member 54 may also be capable of rotating relative to the sleeve 50 about an axis that is parallel to the longitudinal direction. The fixation member 54 can be made from a first material, and the sleeve 50 can be made from a second material. The first material can be stiffer than the second material. For example, the first material can comprise cobalt chromium and the second material can comprise titanium. It should be appreciated, however, that the sleeve 50 and the fixation member 54 can be made from any materials as desired.

Figure 2B:
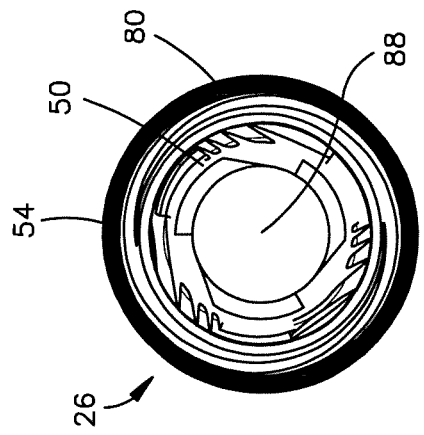
FIG. 2B is a bottom plan view of the dynamic fixation element shown in FIG. 2A.
Figure 2A:
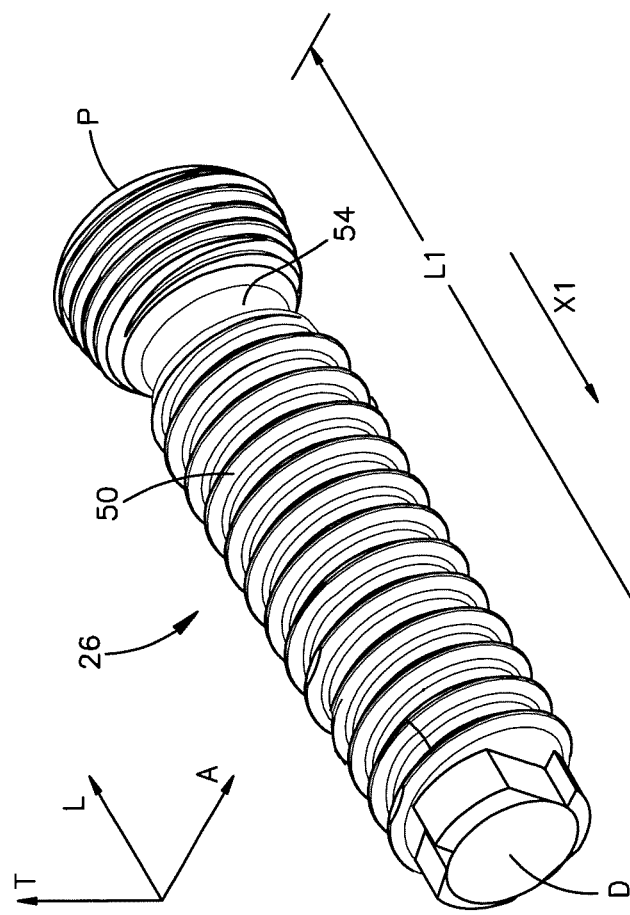
FIG. 2A is a perspective view of a dynamic fixation element according to an embodiment, the dynamic fixation element having a sleeve and a fixation member coupled to the sleeve, the sleeve defines a distal end, a proximal end, and a channel extending from the distal end through to the proximal end, and the fixation member includes a shaft, a head extending from a proximal end of the shaft, and an abutment member extending from a distal end of the shaft, such that the sleeve is captured between the head and the abutment member.

As shown in FIG. 2A, the dynamic bone fixation element 26 is elongate along a first direction $X_1$ (e.g. the longitudinal direction L) and has a proximal end P and a distal end D spaced apart from the proximal end P along the first direction $X_1$. The dynamic bone fixation element 26, and in particular the fixation member 54 can have an overall length $L_1$ measured from the proximal end P to the distal end D along the first direction $X_1$ that is between about 1.0 mm and about 160.0 mm, and for certain embodiments between about 1.0 mm and about 3.0 mm. It should be appreciated, however, that the dynamic bone fixation element can have any length as desired. Therefore, the dynamic bone fixation element 26 can be configured to affix a load carrier to different anatomical structures of different sizes. For example, the dynamic bone fixation element 26 can be configured to affix a load carrier to the mandible or the cervical spine.

As shown in FIGS. 2B-2E, the sleeve 50 is elongate along the first direction $X_1$ and defines a first or proximal end 58 and a second or distal end 62 spaced apart from the proximal end 58 along the first direction $X_1$. The sleeve 50 can have an overall length $L_2$ that is measured from the proximal end 58 to the distal end 62. The sleeve 50 includes at least an inner surface 64 that at least partially defines a channel 66 that extends from the proximal end 58 and toward the distal end 62 along the first direction $X_1$ such that the channel 66 extends through both the proximal end 58 and the distal end 62. As shown in FIG. 2E, the sleeve 50 includes four surfaces 64 that define the channel 66. Therefore, a cross-section of the channel 66 is non-circular. That is, a cross-section of the channel 66 can be polygonal shaped, such as square shaped as illustrated. It should be appreciated, however, that the channel 66 can be defined by any number of inner surfaces 64 and that the cross-section of the channel 66 can have any non-circular shape, as desired. For example, the cross-section of the channel 66 can be hexagonally shaped. Moreover, it should be appreciated that a cross-section of each portion of the channel 66 along the entire length of the channel 66 can be non-circular, or alternatively a cross-section of the channel 66 along only a portion of the length of the channel 66 can be non-circular while a remaining portion of the length of the channel 66 has a circular cross-section. Further, it should be appreciated, that the channel 66 can extend through the proximal end and toward the distal end but not through the distal end.

As shown in FIGS. 2D and 2E, the channel 66 has a cross-sectional dimension $D_1$ that is measured along a direction that is perpendicular to the first direction $X_1$. The dimension $D_1$ can be sized such that the channel 66 receives the fixation member 54 and the fixation member 54 is moveable within the channel 66 along at least a direction that has a directional component that is transverse to the first direction $X_1$. It should be appreciated that the dimension $D_1$ can be the same for the entire length of the channel 66 or the dimension $D_1$ can vary along the length of the channel 66 so long as the fixation member 54 is capable of moving within the channel 66 as described.

The inner surfaces 64 can each define respective stops 67 that are configured to limit the movement of the fixation member 54 within the channel 66. That is, the stops 67 can limit the movement of the fixation member relative to the sleeve along the direction that has a directional component that is transverse to the first direction $X_1$. The stops 67 can be portions of the inner surfaces 64 proximate to the proximal end of the channel 66 or portions proximate to the distal end of the channel 66 as shown in FIG. 2D. It should be appreciated, however, that the stops 67 can be portions of the inner surfaces 64 disposed anywhere along the channel 66, or even the entire inner surfaces 64 of the channel.

As shown in FIGS. 2A-2D, the sleeve 50 further includes an outer surface 70 that extends from the proximal end 58 to the distal end 62 along the first direction $X_1$. The outer surface 70 carries a thread 74 that is configured to engage an anatomical structure such as bone. It should be appreciated, however, that the thread 74 can be configured to engage any anatomical structure as desired. As shown in FIG. 2C, the thread 74 can extend the entire length of the sleeve 50 along the first direction $X_1$. It should be appreciated, however, that the thread 74 can extend only partially along the length of the sleeve 50 as desired. Moreover, it should be appreciated that the thread 74 can comprise a plurality of segments of threads that extend around the sleeve 50 so long as the thread 74 can engage the anatomical structure and affix the dynamic bone fixation element 26 to the anatomical structure.

As shown in FIG. 2D, the sleeve 50 further includes a first or proximal abutment surface 76 and a second or distal abutment surface 78 that faces away from the first abutment surface 76. The first and second abutment surfaces 76 and 78 are configured to abut respective abutment surfaces of the fixation member 54 to thereby limit movement of the fixation member 54 relative to the sleeve 50 along the first direction $X_1$. As shown, the first and second abutment surfaces 76 and 78 can be the proximal and distal ends 58 and 62, respectively, of the sleeve 50. Therefore, the first and second abutment surfaces 76 and 78 can be spaced apart from each other by the distance $L_2$. It should be appreciated, however, that portions of the sleeve 50 can extend proximal to the first abutment surface 76 and distal to the second abutment surface 78 such that the abutment surfaces 76 and 78 are not the proximal and distal ends of the sleeve 50.

As shown in FIGS. 2C and 2D, the fixation member 54 extends into the channel 66 of the sleeve 50 and is loosely coupled to the sleeve 50 such that the fixation member 54 is moveable relative to the sleeve. The fixation member 54 has a head 80, a shaft 84 extending distally from the head 80 along a second direction $X_2$, and an abutment member 88 extending from the shaft 84. A shown, the abutment member 88 can extend from a distal end of the shaft 84 such that the sleeve 50 is captured between the head 80 and the abutment member 88. In this way, the sleeve 50 is coupled to the fixation member 54. It should be appreciated, that the second direction $X_2$ can be parallel to the first direction $X_1$ or can be angularly offset with respect to the first direction $X_1$. It should also be appreciated, that the abutment member 88 can extend from a portion of the shaft that is proximal to the distal end of the shaft 84.

As shown in FIGS. 2C and 2D, the head 80 includes a head body 90 that is circular in cross section and defines a proximal surface 92, a distal surface 94, and a side surface 96 that tapers inward as the side surface 96 extends from the proximal surface 92 to the distal surface 94. The tapered side surface 96 carries a thread 98 that is configured to engage one of the threads 42 of the load carrier 22 as the dynamic bone fixation element 26 is inserted through one of the bone fixation holes 38 of the load carrier 22. Once the thread 98 has engaged the thread 42, the dynamic bone fixation element 26 will be locked to the load carrier 22. While the head 80 includes a thread 98 in the illustrated embodiment, it should be appreciated that the head can be devoid of threads. Moreover, it should be appreciated that the side surface 96 can taper radially outward as the side surface 96 extends from the proximal surface 92 to the distal surface 94, or the side surface 96 can be void of taper and can be substantially perpendicular to the proximal and distal surfaces 92 and 94.

As shown in FIG. 2D, the head 80 further includes a mating member 102 that extends into the proximal surface 92 of the head 80. The mating member 102 is configured to engage a corresponding mating member of a driving tool. The mating member 102 can be a hexagonal shaped recess 106 that is configured to be engaged by a hexagonal protrusion of the driving tool such that as the driving tool is rotated the dynamic bone fixation element 26 will be rotated and driven into the anatomical structure. It should be appreciated, however, that the mating member 102 can include other configurations as desired, so long as the mating member 102 can mate with the driving tool to thereby impart rotation to the dynamic bone fixation element 26. For example, the mating member 102 can be a slot shaped recess.

As shown in FIG. 2D, the distal surface 94 of the head 80 extends radially out from the shaft 84 so as to define a shoulder 110 that has a first abutment surface 114. The shoulder 110 has a cross-sectional dimension $D_2$ measured along a direction that is perpendicular to the second direction $X_2$. The cross-sectional dimension $D_2$ of the shoulder 110 is greater than the cross-sectional dimension $D_1$ of the channel 66. As shown in FIG. 2D, the first abutment surface 114 faces the first abutment surface 76 of the sleeve 50 and is configured to abut the first abutment surface 76 of the sleeve 50 so as to limit distal movement of the fixation member 54 relative to the sleeve 50 along the first direction $X_1$.

While in the illustrated embodiment, the head 80 is configured to affix a bone plate to an anatomical structure, it should be appreciated that the head 80 can have other configurations to affix other load carriers to an anatomical structure. For example, the head 80 can be configured to define a channel that receives a spinal rod. In such an embodiment, the channel can extend through the head along a direction that is perpendicular to the second direction $X_2$ and can have an opening such that the channel can receive the rod along the second direction $X_2$. It should be appreciated, however, that the channel can have an opening such that the channel can receive the rod along a direction that is perpendicular to the second direction $X_2$.

As shown in FIG. 2D, the shaft 84 extends distally from the distal surface 94 of the head 80. The shaft 84 can have an overall length $L_3$ that is greater than or substantially equal to the overall length $L_2$ between the first and second abutment surfaces of the sleeve 50. Therefore, the shaft 84 can be configured to extend completely through the channel 66 of the sleeve 50 such that a proximal end of the shaft 84 is proximal to the proximal end of the channel 66 and a distal end of the shaft 84 is distal to the distal end of the channel 66. It should be appreciated, however, that in some cases the shaft 84 can have an overall length $L_3$ that is less than the overall length $L_2$ of the sleeve 50. For example, in some embodiments the abutment member can extend from the shaft such that a portion of the abutment member is within the channel 66 of the sleeve 50 (see for example FIG. 5A).

As shown in FIGS. 2D and 2E, the shaft 84 includes at least an outer surface 120 that faces the inner surface 64 of the channel 66. As shown in FIG. 2E, the shaft 84 includes four outer surfaces 120 that each faces a respective inner surface 64 of the channel 66. Therefore, the shaft 84 can have a cross-section that is non-circular. That is, a cross-section of the shaft 84 can be polygonal shaped, such as square shaped as illustrated. It should be appreciated, however, that the shaft 84 can be defined by any number of outer surfaces 120 and that the cross-section of the shaft 84 can have any non-circular shape, as desired. For example, the cross-section of the shaft 84 and the channel 66 can be hexagonally shaped as shown in FIG. 2H. Moreover, it should be appreciated that a cross-section of each portion of the shaft 84 along the entire length of the shaft 84 can be non-circular, or alternatively a cross-section of the shaft 84 along only a portion of the length of the shaft 84 can be non-circular while a remaining portion of the length of the shaft 84 has a circular cross-section. Because the shaft 84 is non-circular and the channel 66 is non-circular, the sleeve 50 will rotate as the fixation member 54 is rotated. That is, as the fixation member 54 is rotated, the outer surfaces 120 of the shaft 84 will contact the inner surfaces 64 of the sleeve 50 to thereby cause the sleeve 50 to rotate and be driven into the anatomical structure. Therefore, the sleeve 50 does not have to be rigidly coupled (i.e. welded) to the fixation member 54 in order for the sleeve 50 to rotate as the fixation member 54 is rotated. It should be appreciated, however, that in some embodiments the shaft 84 and the channel 66 can have circular cross-sections. For example, the shaft 84 or the channel 66 can include features that engage each other such that as the fixation member 54 is rotated, the sleeve 50 will rotate.

As shown in FIGS. 2D and 2E, the outer surfaces 120 of the shaft 84 each faces a respective inner surface 64 of the channel 66 such that respective non-zero gaps 130 are defined between the outer surfaces 120 and the inner surfaces 64. As shown, at least a portion of the shaft 84 that is within the channel 66 has a cross-sectional dimension $D_3$ measured along a direction perpendicular to the second direction $X_2$ that is less than the cross-sectional dimension $D_1$ of the channel 66. Therefore the fixation member 54 is received by the channel 66 such that the fixation member 54 is moveable within the channel 66 along at least a direction that has a directional component that is transverse to the first direction $X_1$. In particular, the fixation member is moveable relative to the sleeve 50 along a plurality of directions, each direction of the plurality of directions having a directional component that is transverse to the first direction $X_1$. It should be appreciated that the dimension $D_3$ can be the same for the entire length of the shaft 84 or the dimension $D_3$ can vary along the length of the shaft 84 so long as the fixation member 54 is capable of moving within the channel 66 as described. It should also be appreciated that the cross-sectional dimension $D_1$ and the cross-sectional dimension $D_3$ preferably are measured along the same direction.

In another embodiment and in reference to FIG. 2F, the sleeve 50 can be configured to restrict movement of the fixation member 54 relative to the sleeve in one plane. As shown in FIG. 2F, the sleeve 50 can include two parallel first surfaces 64a and two parallel second surfaces 64b that are longer than the first surfaces 64a and together define a channel 66a. Therefore, a cross-section of the channel 66a is rectangular shaped. That is, the channel 66a has a first cross-sectional dimension $D_5$ that is measured between the first surfaces 64a along a direction that is perpendicular to the first direction $X_1$ and a second cross-sectional dimension $D_6$ that is measured between the second surfaces 64b along a direction that is perpendicular to both the first direction and the direction in which the first cross-sectional dimension $D_5$ is measured. As shown, the second cross-sectional dimension $D_6$ is greater than the first cross-sectional dimension $D_5$.

As shown in FIG. 2F, the first cross-sectional dimension $D_5$ of the channel 66a is substantially equal to the cross-sectional dimension $D_3$ of the shaft 84, and the second cross-sectional dimension $D_6$ of the channel 66a is greater than the cross-sectional dimension $D_3$ of the shaft 84. Therefore, the fixation member 54 is moveable relative to the sleeve 50 in a first plane that is perpendicular to the first direction $X_1$ and is fixed relative to the sleeve 50 in a second plane that is perpendicular to both the first direction $X_1$ and the first plane.

Referring back to FIGS. 2C and 2D, the abutment member 88 extends from a distal end of the shaft 84 and includes an abutment member body 160 that is circular in cross section and defines a proximal surface 162, a distal surface 164, and a side surface 166 that extends from the proximal surface 162 to the distal surface 164. As shown in FIG. 2D, the proximal surface 162 of the abutment member 88 extends radially out from the shaft 84 so as to define a shoulder 170 that has a second abutment surface 174 that faces the first abutment surface 114 of the head 80. The shoulder 170 has a cross-sectional dimension $D_4$ measured along a direction that is perpendicular to the second direction $X_2$ that is greater than the cross-sectional dimension $D_1$ of the channel 66. The second abutment surface 174 faces the second abutment surface 78 of the sleeve 50 and is configured to abut the second abutment surface 78 of the sleeve 50 so as to limit proximal movement of the fixation member 54 along the first direction $X_1$.

As shown in FIG. 2G, the sleeve 50 is captured between the head 80 and the abutment member 88. As shown, at least a portion of the sleeve 50, such as the entire sleeve 50, can be captured between the shoulder 110 of the head 80 and the shoulder 170 of the abutment member 88 such that the fixation member 54 is substantially fixed relative to the sleeve 50 along the first direction $X_1$. The sleeve 50 can also be captured between the shoulder 110 of the head 80 and the shoulder 170 of the abutment member 88 such that the fixation member 54 is moveable relative to the sleeve 50 along the first direction $X_1$. Therefore, the first and second abutment surfaces 114 and 174 can be spaced from each other along the second direction $X_2$ such that a length $L_4$ is defined between the first and second abutment surfaces 114 and 174 that is either substantially equal to or greater than the overall length $L_1$ of the sleeve 50. In cases where the length $L_4$ is greater than the length $L_1$ a variable sized gap can be defined between at least one of the sleeve 50 and the head 80 and/or the sleeve 50 and the abutment member 88 (see for example FIG. 5A) to thereby permit movement of the fixation member 54 relative to the sleeve 50 along the first direction $X_1$.

Referring to FIG. 2G, the fixation member 54 is coupled to the sleeve 50 such that the head 80 is moveable along a third direction $X_3$ and the abutment member 88 is moveable along a fourth direction $X_4$. Both the third direction $X_3$ and the fourth direction $X_4$ have a directional component that is perpendicular to the first direction $X_1$. It could also be said that the fixation member 54 is coupled to the sleeve 50 such that a proximal end of the fixation member 54 is moveable along the third direction $X_3$ and a distal end of the fixation member is moveable along the fourth direction $X_4$. Therefore, depending on the configuration of the dynamic bone fixation element, each portion of the fixation member 54 may be moveable relative to the sleeve 50. Because the fixation member 54 is moveable along the first direction $X_1$, the third direction $X_3$, and the fourth direction $X_4$ relative to the sleeve 50, the fixation element 26 has improved stress dispersion and allows for micro-movement to thereby improve the quality of the bone being generated.

The third and fourth directions $X_3$ and $X_4$ can be substantially the same direction or directions that are substantially opposite to each other. For example, when the third and fourth directions $X_3$ and $X_4$ are substantially the same direction the fixation member 54 moves relative to the sleeve 50 such that proximal and distal portions of the shaft 84 contact or are otherwise limited by stops 67 of the same inner surface 64 of the channel 66. Alternatively, when the third and fourth directions $X_3$ and $X_4$ are substantially opposite to each other, the fixation member 54 moves relative to the sleeve 50 such that a proximal portion of the shaft 84 contacts or is otherwise limited by a proximal stop 67 of a first inner surface 64 of the channel 66 and a distal portion of the shaft 84 contacts or is otherwise limited by a distal stop 67 of a second inner surface 64 that is opposed to and faces the first inner surface 64. It should be appreciated, however, that the fixation member 54 can move such that the shaft 84 flexes and the head 80 moves relative to the abutment member 88. For example, when in use, the abutment member 88 may not be moveable and may be limited by the anatomical structure to which the dynamic bone fixation element is affixed. In such a case, the shaft 84 may flex and the head 80 may move relative to the sleeve 50 and the abutment member 88.

When the third and fourth directions $X_3$ and $X_4$ are substantially opposite to each other, the direction in which the shaft 84 extends (i.e. the second direction $X_2$) may be angularly offset with respect to a center axis C of the channel 66. For example, as shown in FIG. 2G, the fixation member 54 may be moveable with respect to the sleeve 50 such that shaft 84 extends at an angle Ø with respect to the center axis C. The angle Ø can be any angle between about 0 degrees and about 50 degrees. It should be appreciated however, that the angle Ø may be any angle as desired and may depend on the size of the shaft 84 and/or the size of the channel 66.

The fixation member 54 may also be moveable with respect to the sleeve 50 along the first direction $X_1$ such that a variable gap is defined between the abutment surface of the head 80 and the first abutment surface of the sleeve 50, and between the abutment surface of the abutment member 88 and the second abutment surface of the sleeve 50. The variable angle gaps can be equal to or greater than zero. Therefore, the fixation member 54 can be moveable relative to the sleeve 50 along a plurality of directions each direction having a directional component that is either perpendicular to or parallel to the first direction $X_1$.

Now referring to FIG. 2H, the fixation member 54 may also rotate relative to the sleeve 50 about the central axis C. The fixation member 54 can rotate either clockwise or counter-clockwise. As shown, because both the shaft 84 and the channel 66 are polygonal shaped rotation of the fixation member 54 can be limited. That is, the fixation member 54 may be limited to rotating a specified angle relative to the sleeve 50. For example, the fixation member 54 may be limited to rotating 30 degrees as illustrated. It should be appreciated, however, that the fixation member 54 and the sleeve 50 can be configured such that the fixation member 54 can rotate any angle relative to the sleeve 50 as desired. Therefore, the fixation member 54 can have up to six degrees of freedom relative to the sleeve 50.

In operation and in reference to FIG. 1, the load carrier 22 can be affixed to first and second bone portions across a bone gap defined between the first and second bone portions. The load carrier 22 can be positioned such that at least one fixation hole 38 is aligned with the first bone portion 14a, and at least one fixation hole 38 is aligned with the second bone portion 14b. A first dynamic bone fixation element 26a can be inserted through one of the fixation holes 38 such that the sleeve 50 engages the first bone portion 14a and the threads of the head 80 engage the threads of the fixation hole 38. Similarly, a second dynamic bone fixation element 26b can be inserted through one of the fixation holes 38 such that the sleeve 50 engages the second bone portion 14b and the threads of the head 80 engage the threads of the fixation hole 38. By using the dynamic bone fixation elements 26, micro-movement of the first and second bone portions 14a and 14b is permitted along multiple directions including the longitudinal direction so as to promote fusion of the first and bone portions 14a and 14b. The first and second bone portions 14a and 14b can be mandibular bone portions or vertebral bodies of the cervical spine. It should be appreciated, however, that the first and second bone portions 14a and 14b can be any bone portions or anatomical structures found in a body.

Now in reference to FIGS. 3 and 4, the fixation member 54 can be coupled to the sleeve 50 using a variety of manufacturing techniques. In each case, the fixation member 54 can be loosely coupled (i.e. not welded) to the sleeve 50. That is, all portions of the fixation member 54 can be moveable relative to the sleeve 50. For example, both the proximal end and the distal end of the fixation member 54 can be moveable with respect to the sleeve 50 along a direction that has a directional component perpendicular to the first direction $X_1$ when the fixation member 54 is coupled to the sleeve 50. It should be appreciated, however, that in use, a distal portion of the fixation member 54 may be fixed relative to the sleeve 50.

As shown in FIG. 3, the fixation member 54 can be initially formed such that the head 80 is separate from an integrally formed or otherwise monolithic shaft 84 and abutment member 88. To assemble the dynamic bone fixation element 26, the shaft 84 can be inserted into a distal end of the channel 66 and translated along the longitudinal direction L toward the proximal end of the channel 66 until the abutment surface 174 abuts the second abutment surface 68 of the sleeve 50. Once inserted, the head 80 having the abutment surface 114 can be coupled to the proximal end of the shaft 84 by a weld to thereby capture the sleeve 50 between the abutment surfaces 114 and 174 of the head 80 and the abutment member 88, respectively. It should be appreciated, however, that the dynamic bone fixation element 26 can be assembled other ways so long as the shaft 84 is integrally formed with a first abutment surface and a second abutment surface can be coupled to the shaft at a later time. For example, it should be appreciated that the head 80 and the shaft 84 can be integrally formed while the abutment member 88 is separate. In such a case, the shaft 84 is inserted through a proximal end of the channel 66 and translated along the longitudinal direction L toward the distal end of the channel 66 until the abutment surface 114 abuts the first abutment surface 76 of the sleeve 50. Once inserted, the abutment member 88 having the abutment surface 174 can be coupled to the distal end of the shaft 84 by a weld. It should also be appreciated that the head 80 or the abutment member 88 can be coupled to the shaft 84 without using a weld. For example, the head 80 or the abutment member 88 can be coupled to the shaft 84 with a locking or snap feature formed on the head 80, the shaft 84, and/or the abutment member 88.

As shown in FIG. 4, the sleeve 50 can also be overmolded onto the fixation member 54. In such a case, the fixation member 54 can be monolithic or otherwise integrally formed as a single unit and the sleeve 50 can be overmolded onto the shaft 84. That is, the head 80, the shaft 84, and the abutment member 88 can be integral to each other and the sleeve 50 can be overmolded onto the shaft 84 using a mold 200. As shown in FIG. 4, the mold 200 can include an upper die and a lower die 204. One of the dies may be moveable with respect to the other, or both dies may be movable with respect to teach other. The upper and lower dies can be identically constructed unless otherwise indicated, such that the mold can be formed by inverting the upper die and joining the upper die with the lower die 204. Accordingly, though the lower die 204 is described in detail herein, it should be appreciated that the descriptions of the lower die 204 applies to the upper die unless otherwise indicated.

The lower die 204 includes a top surface 208 that defines an engagement surface 212 configured to engage the complementary engagement surface of the upper die. The lower die 204 further defines a pocket 216 that extends from the engagement surface 212 vertically into the die 204. The pocket 216 is configured to receive the shaft 84 and defines a portion such as a first half of the sleeve 50 surrounding half of the shaft 84. As shown, the pocket 216 has an outer wall 218 that is shaped to correspond to the shape of the outer wall of the sleeve 50. The pocket 216 of the lower die 204 can be combined with the complementary pocket of the upper die to form a corresponding mold cavity when the dies are brought together. The mold cavity can define the sleeve 50 around the entire shaft 84.

The lower die 204 further includes at least one injection conduit section 230 having a channel 234 that defines a terminal end defining an injection port 238 that extends through the outer wall 218 of the pocket 216. The channel 234 is configured to receive a mold material and direct the mold material into the cavity formed by the upper and lower dies. The injection molding material conforms to the shaft and the pockets to thereby form the sleeve 50 as described above.

To ensure that a gap is formed between the outer surfaces of the shaft 84 and the inner surfaces of the channel 66 of the sleeve 50, a filler material 220 can be disposed between the shaft and the die 204. For example, the filler material 220 can be a wax disposed on the shaft 84 that can be subsequently removed after the sleeve 50 has been formed to thereby permit the fixation member 54 to move within the channel 66 of the sleeve 50. It should be appreciated, however, that the filler material can have other configurations. For example, the filler material can be sand.

It should be appreciated that the fixation element 26 can be manufactured using any technique as desired. For example, the sleeve 50 can also be formed or otherwise coupled to the fixation member 54 through 3-D metal printing, such as selective laser sintering. A selective laser sintering system can include a high power laser such as a carbon dioxide laser that is configured to fuse small particles of metal into a mass that has a desired 3-D shape (i.e. the shape of the sleeve 50). Therefore, to form the sleeve 50, a digital file containing a 3-D description of the sleeve 50 can be downloaded or otherwise transferred to the system. As the process begins, a thin first layer of powdered material can be spread across a build platform of the system. Then using data from the 3-D digital description, the laser will selectively draw a cross section of the sleeve 50 on the first layer of powdered material. As the laser draws the cross-section, it selectively sinters (heats and fuses) the powdered material to thereby create a solid mass that represents a first cross-section of the sleeve 50. The system continues this process until the sleeve 50 is complete.

Now in reference to FIGS. 5A-5D, the fixation member can be constructed such that the dynamic bone fixation element 26 can be assembled manually without the use of a mold or weld. As shown in FIGS. 5A-5D, a dynamic bone fixation element 326 includes a sleeve 350 and a fixation member 354 loosely coupled to the sleeve 350. The sleeve 350 and the fixation member 354 are identical to the sleeve 50 and the fixation member 54 shown in FIGS. 2A-2E and include like structure unless otherwise described. Moreover, the dynamic bone fixation element 326 operates and functions in a similar manner as the dynamic bone fixation element 26 unless otherwise described.

Figure 5A:
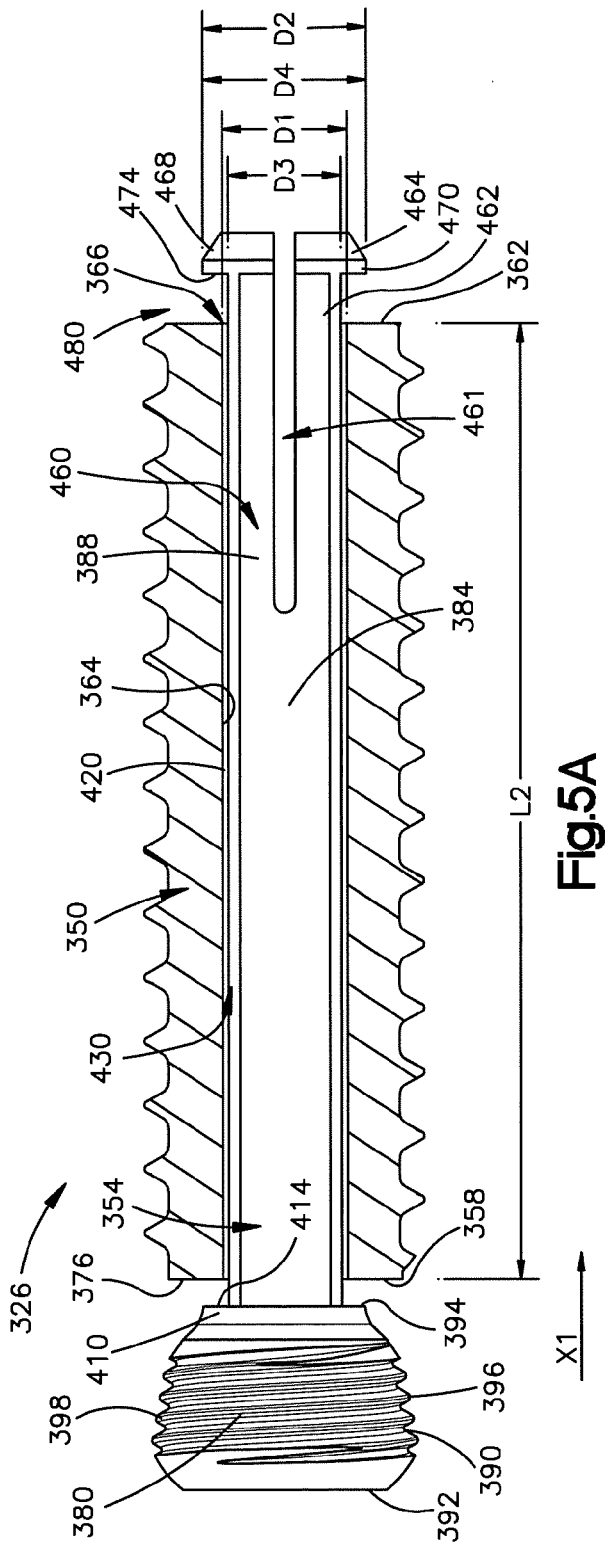
FIG. 5A is a perspective view of a dynamic fixation element in accordance with another embodiment, the dynamic fixation element having a sleeve and a fixation member that includes an abutment member that comprises four flexible extensions that flex inward as the shaft of the fixation member advances through a channel of the sleeve.

As shown in FIG. 5A the sleeve 350 is elongate along the first direction $X_1$ and defines a first or proximal end 358 and a second or distal end 362 spaced apart from the proximal end 358 along the first direction $X_1$. The sleeve 350 can have an overall length $L_2$ that is measured from the proximal end 358 to the distal end 362 along the first direction $X_1$. The sleeve 350 includes an inner surface 364 that at least partially defines a channel 366 that extends from the proximal end 358 toward the distal end 362 along the first direction $X_1$ such that the channel 366 extends through both the proximal end 358 and the distal end 362. As shown, the channel 366 has a cross-sectional dimension $D_1$ that is measured along a direction that is perpendicular to the first direction $X_1$. The dimension $D_1$ of the channel 366 can receive the fixation member 354 such that the fixation member 354 is moveable within the channel 366 along at least a direction that has a directional component that is transverse to the first direction $X_1$.

As shown, the sleeve 350 further includes a first or proximal abutment surface 376 and a second or distal abutment surface 378 that faces away from the first abutment surface 376. The first and second abutment surfaces 376 and 378 are configured to abut respective abutment surfaces of the fixation member 354 to thereby limit movement of the fixation member 354 relative to the sleeve 350 along the first direction $X_1$. As shown, the first and second abutment surfaces 376 and 378 can be the proximal and distal ends 358 and 362, respectively, of the sleeve 350. Therefore, the first and second abutment surfaces 376 and 378 can be spaced apart from each other by the length $L_2$ along the first direction $X_1$. It should be appreciated, however, that portions of the sleeve 350 can extend proximal to the first abutment surface 376 and distal to the second abutment surface 378 such that the abutment surfaces 376 and 378 are not the absolute proximal and distal ends of the sleeve 350.

Figure 5B:
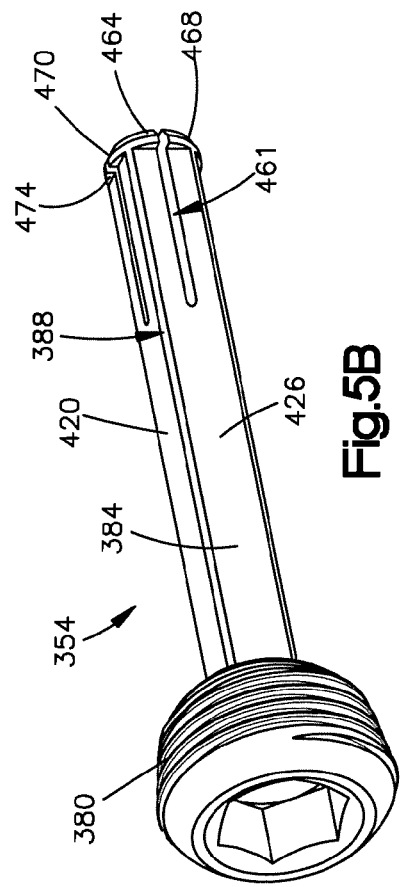
FIG. 5B is a perspective view of the fixation member shown in FIG. 5A.

As shown in FIG. 5A, the fixation member 354 extends through the channel 366 of the sleeve 350 along the first direction $X_1$. As shown in FIGS. 5B and 5C, the fixation member 354 has a head 380, a shaft 384 extending distally from the head 380 along a second direction $X_2$, and an abutment member 388 extending from the shaft 384. As shown, the abutment member 388 can extend from a distal end of the shaft 384 such that at least a portion of the abutment member 388 extends along a direction that is perpendicular to the second direction $X_2$ and the sleeve 350 is captured between the head 380 and the abutment member 388. In this way, the sleeve 350 is coupleable to the fixation member 354.

As shown in FIGS. 5B and 5C, the head 380 includes a head body 390 that is circular in cross section and defines a proximal surface 392, a distal surface 394, and a side surface 396 that tapers inward as the side surface 396 extends from the proximal surface 392 to the distal surface 394. The tapered side surface 396 carries a thread 398 that is configured to engage one of the threads 42 of the load carrier 22 as the dynamic bone fixation element 326 is inserted through one of the bone fixation holes 38 of the load carrier 22. Once the thread 398 has engaged the thread 42, the dynamic bone fixation element 326 will be locked to the load carrier 22.

As shown in FIGS. 5A and 5C, the distal surface 394 of the head 380 extends radially out from the shaft 384 so as to define a shoulder 410 that has a first abutment surface 414. The shoulder 410 has a cross-sectional dimension $D_2$ measured along a direction that is perpendicular to the second direction $X_2$. The cross-sectional dimension $D_2$ of the shoulder 410 is greater than the cross-sectional dimension $D_1$ of the channel 366. As shown in FIG. 5A, the first abutment surface 414 faces the first abutment surface 376 of the sleeve 350 and is configured to abut the first abutment surface 376 of the sleeve 350 so as to limit distal movement of the fixation member 354 along the first direction $X_1$.

As shown in FIG. 5C, the shaft 384 extends distally from the distal surface 394 of the head 380. The shaft 384 includes at least an outer surface 420 that faces the inner surface 364 of the channel 366. Like the dynamic bone fixation element 26, the fixation member 354 and the sleeve 350 are configured such that as the fixation member 354 is rotated, the outer surfaces 420 of the shaft 384 will contact the inner surfaces 364 of the sleeve 350 to thereby cause the sleeve 350 to rotate and be driven into the anatomical structure. Therefore, the sleeve 350 does not have to be rigidly connected (i.e. welded) to the fixation member 354.

As shown in FIG. 5A, the outer surfaces 420 of the shaft 384 each face a respective inner surface 364 of the channel 366 such that respective non-zero gaps 430 are defined between the outer surfaces 420 and the inner surfaces 364. Therefore, at least a portion of the shaft 384 that is within the channel 366 has a cross-sectional dimension $D_3$ measured along a direction perpendicular to the second direction $X_2$ that is less than the cross-sectional dimension $D_1$ of the channel 366. Therefore the fixation member 354 is received by the channel 366 such that the fixation member 354 is moveable within the channel 366 along at least a direction that has a directional component that is transverse to the first direction $X_1$. In particular, the fixation member 354 is moveable relative to the sleeve 350 along a plurality of directions, each direction of the plurality of directions having a directional component that is transverse to the first direction $X_1$. It should be appreciated that the dimension $D_3$ can be the same for the entire length of the shaft 384 or the dimension $D_3$ can vary along the length of the shaft 384 so long as the fixation member 354 is capable of moving within the channel 366 as described.

As shown in FIGS. 5A-5D, the abutment member 388 extends from a distal end of the shaft 384 and includes at least one such as four flexible extensions 460 that are separated from each other by elongate slots 461 and are configured to resiliently flex inward as the shaft 384 is passed through the channel 366 during assembly of the dynamic bone fixation element 326. Each flexible extension 460 includes an elongate body 462 and a shelf 464 that extends radially outward from a distal portion of the body 462 along a direction that is perpendicular to the second direction. The shelves 464 together define a shoulder 470 that has a second abutment surface 474 that faces the first abutment surface 414 of the head 380. The abutment member 388 or at least the shoulder 470 has a cross-sectional dimension $D_4$ measured along a direction that is perpendicular to the second direction $X_2$ that is greater than the cross-sectional dimension $D_1$ of the channel 366. The second abutment surface 474 faces the second abutment surface 378 of the sleeve 350 and is configured to abut the second abutment surface 378 of the sleeve 350 so as to limit proximal movement of the fixation member 354 along the first direction $X_1$.

As shown in FIG. 5C each shelf 464 further includes an outer surface 468 that tapers inward from a proximal surface of the shelf 464 to a distal surface of the shelf 464. Each tapered surface 468 is configured to engage the inner surfaces 364 of the channel 366 to thereby force the flexible extensions 460 inward as the shaft 384 is passed through the channel 366. It should be appreciated, however, that the outer surfaces 468 do not have to be tapered and can have other configurations as desired. For example, the outer surfaces 468 can be perpendicular to the proximal surface of the shelf 464.

As shown in FIG. 5A, at least a portion such as the entire sleeve 350 is captured between the shoulder 410 of the head 380 and the shoulder 470 of the abutment member 388 such that the portion of the sleeve 350 is aligned with the abutment surface 474 of the abutment member 388 along the first direction. As shown, the sleeve 350 can be captured between the shoulder 410 of the head 380 and the shoulder 470 of the abutment member 388 such that the fixation member 354 is moveable relative to the sleeve 350 along the first direction $X_1$, or the sleeve 350 can be captured between the shoulder 410 of the head 380 and the shoulder 470 of the abutment member 388 such that the fixation member 354 is substantially fixed relative to the sleeve 350 along the first direction $X_1$. Therefore, the first and second abutment surfaces 414 and 474 can be spaced from each other along the second direction $X_2$ such that a length $L_{C3}$ is defined between the first and second abutment surfaces 414 and 474 that is either substantially equal to or greater than the overall length $L_2$ between the first and second abutment surfaces 376 and 378 of the sleeve 350.

As shown in FIG. 5A, in cases where the length $L_{C3}$ is greater than the length $L_2$ a variable sized gap 480 can be defined between at least one of the sleeve 350 and the head 380 and/or the sleeve 350 and the abutment member 388. In particular, the variable sized gaps 480 can be defined between the abutment surface of the head 380 and the first abutment surface 376 of the sleeve 350, and/or the abutment surface of the abutment member 388 and the second abutment surface 378 of the sleeve 350. The variable sized gaps 480 can be measured along a direction that is parallel to the first direction $X_1$ and can vary between about 0 mm and about 0.4 mm. It should be appreciated, however, that the variable sized gaps 480 can vary between any desired distances. It should be further appreciated, that when the gap 480 between the head 380 and the sleeve 350 decreases, the gap 480 between the abutment member 388 and the sleeve 350 increases, and vice versa.

The fixation member 354 is coupled to the sleeve 350 by inserting the abutment member 388 into a proximal end of the channel 366 such that the tapered surfaces 468 of the shelves 464 contact the inner surfaces 364 of the channel to thereby flex or otherwise force the flexible extension inward from a first position to a flexed second position. The flexible extensions 460 will remain flexed as the shaft 384 is passed through the channel 366. Once the shelves 464 have passed through the channel 366 and are distal to the sleeve 350, the flexible extensions 460 will return to the first position or at least substantially close to the first position so as to capture the sleeve 350 between the first and second abutment surfaces 414 and 474. Therefore the abutment member 388 can define an outer surface that has a first cross-section dimension along the second direction when the abutment member 388 is in the channel 366, and the outer surface can define a second cross-sectional dimension along the second direction that is greater than the first cross-sectional dimension when the abutment member 388 is distal to the channel 366. Therefore, the abutment member 388 is resilient such that the outer surface is compressed when in the channel 366 and expanded when distal to the channel 366.

Now in reference to FIGS. 6A-6D, a sleeve 550 constructed in accordance with another embodiment can be configured to be loosely coupled to a fixation member, such as fixation member 354. As shown in FIG. 6A the sleeve 550 is elongate along the first direction $X_1$ and defines a first or proximal end 558 and a second or distal end 562 spaced apart from the proximal end 558 along the first direction $X_1$. The sleeve 550 can have an overall length $L_2$ that is measured from the proximal end 558 to the distal end 562 along the first direction $X_1$. The sleeve 550 includes a channel 565 that extends from the proximal end 558 and toward the distal end 562 along the first direction $X_1$. In particular the sleeve 550 includes a first inner surface 564 that at least partially defines a first portion 566 of the channel 565, and a second inner surface 568 that at least partially defines a second portion 570 of the channel 565 that extends from a distal end of the first portion 566 and toward the distal end 562 along the first direction $X_1$. Therefore it can be said that the channel 565 includes first and second portions 566 and 570. As shown, the first portion 566 of the channel 565 has a cross-sectional dimension $D_7$ that is measured along a direction that is perpendicular to the first direction $X_1$ and the second portion 570 of the channel 565 has a second cross-sectional dimension $D_8$ that is also measured along a direction that is perpendicular to the first direction $X_1$ and is greater than the cross-sectional dimension of the first portion 566 of the channel 565.

The first portion 566 of the channel 565 has a length $L_{C1}$ along the first direction $X_1$ and the second portion 570 of the channel 565 has a second length $L_{C2}$ along the first direction. The length $L_{C1}$ and the dimension $D_7$ of the first portion 566 is configured so that the channel 565 can receive the fixation member 354 such that the fixation member 354 is moveable within the channel 566 along at least a direction that has a directional component that is transverse to the first direction $X_1$. The dimension $D_8$ of the second portion 570 of the channel 565 is configured such that the second portion 570 can receive the shelves 464 of the fixation member 354 so as to couple the fixation member 354 to the sleeve 550. The dimension $D_8$ can be large enough to allow the distal end of the fixation member 354 to move along a direction that is perpendicular to the first direction $X_1$.

As shown in FIG. 6B, the sleeve 550 includes four surfaces 564 that define the first portion 566. Therefore, a cross-section of the first portion 566 is non-circular. That is, a cross-section of the first portion 566 can be polygonal shaped, such as square shaped as illustrated. It should be appreciated, however, that the first portion 566 can be defined by any number of inner surfaces 564 and that the cross-section of the first portion 566 can have any non-circular shape, as desired. For example, the cross-section of the first portion 566 can be hexagonally shaped. Moreover, it should be appreciated that a cross-section of each portion of the first portion 566 along the entire length of the first portion 566 can be non-circular, or alternatively a cross-section of the first portion 566 along only a portion of the length of the first portion 566 can be non-circular while a remaining portion of the length of the first portion 566 has a circular cross-section.

The shelves 464 can be received by the second portion 570 such that the fixation member 354 is fixed in the first direction, or the shelves 464 can be received by the second portion 570 such that fixation member 354 is moveable within the channel 565 along the first direction. For example, the sleeve 550 further includes a first or proximal abutment surface 576 and a second or distal abutment surface 578 that are configured to abut respective abutment surfaces of the fixation member 354 to thereby limit movement of the fixation member 354 relative to the sleeve 550 along the first direction $X_1$. As shown, the first and second abutment surfaces 376 and 378 can be the proximal and distal ends 358 and 362, respectively, of the second portion 570. That is, the first and second abutment surfaces 576 and 578 can at least partially define the second portion 570 and oppose each other along the first direction. Therefore, the first and second abutment surfaces 376 and 378 can be spaced apart from each other by the second length $L_{C2}$ along the first direction $X_1$. The shelves 464 of the abutment member 388 can have a length $L_M$ along the first direction $X_1$ that is less than the second length $L_{C2}$ to thereby allow the fixation member 354 to move along the first direction $X_1$.

As shown in FIG. 6C, the sleeve 550 further includes an outer surface 580 that extends from the proximal end 558 to the distal end 562 along the first direction $X_1$. The outer surface 580 carries a thread 582 that is configured to engage an anatomical structure such as bone. It should be appreciated, however, that the thread 582 can be configured to engage any anatomical structure as desired. As shown in FIG. 6C, the thread 582 can extend the entire length of the sleeve 550 along the first direction $X_1$. It should be appreciated, however, that the thread 582 can extend only partially along the length of the sleeve 550 as desired. Moreover, it should be appreciated that the thread 582 can comprise a plurality of segments of threads that extend around the sleeve 550 so long as the thread 582 can engage the anatomical structure and affix the dynamic bone fixation element to the anatomical structure.

As shown in FIG. 6C, the sleeve can further include cutting flutes 586 proximate to the distal end 562. Therefore as the fixation element is rotated the cutting flutes 586 will cut into the anatomical structure to thereby advance the sleeve 550 into the anatomical structure.

The fixation member 354 can be coupled to the sleeve 550 by inserting the abutment member 388 into a proximal end of the channel 565 such that the tapered surfaces 468 of the shelves 464 contact the inner surfaces 564 of the first portion 566 of the channel 365 to thereby resiliently flex or otherwise force the flexible extensions inward from a first position to a flexed second position. The flexible extensions 460 will remain flexed as the shaft 384 is passed through the first portion 566. Once the shelves 464 have passed through the first portion 566 and into the second portion 570, the flexible extensions 460 will return to the first position or at least substantially close to the first position so as to capture the sleeve 550 between at least the abutment surface 474 and the head 380. Depending on the length $L_{C2}$ of the second portion 570, the length of the shaft 384, and the length $L_M$ of the shelves 464, the fixation member 354 may be configured to move along the first direction.

The abutment surfaces 576 and 578 can be configured to limit the movement of the fixation member 354 along the first direction. It should be appreciated, however, that in some embodiments the proximal end of the sleeve 550 can define an abutment surface. In such embodiments, the proximal end of the sleeve 550 and the proximal abutment surface 576 are configured to limit the movement of the fixation member 354 along the first direction. Therefore, it can be said that at least a portion of the sleeve 550 is captured between the abutment surface 474 of the abutment member 388 and the head 380 along the first direction $X_1$. In embodiments where the captured portion of the sleeve 550 defines a first length (i.e. the length $L_{C1}$ of the first portion 566), and the fixation member 354 defines a second length (i.e. $L_{C3}$) between the head 380 and the abutment surface 474 of the abutment member 388 that is greater than the first length, the fixation member may be moveable along the first direction $X_1$.

Figure 7A:
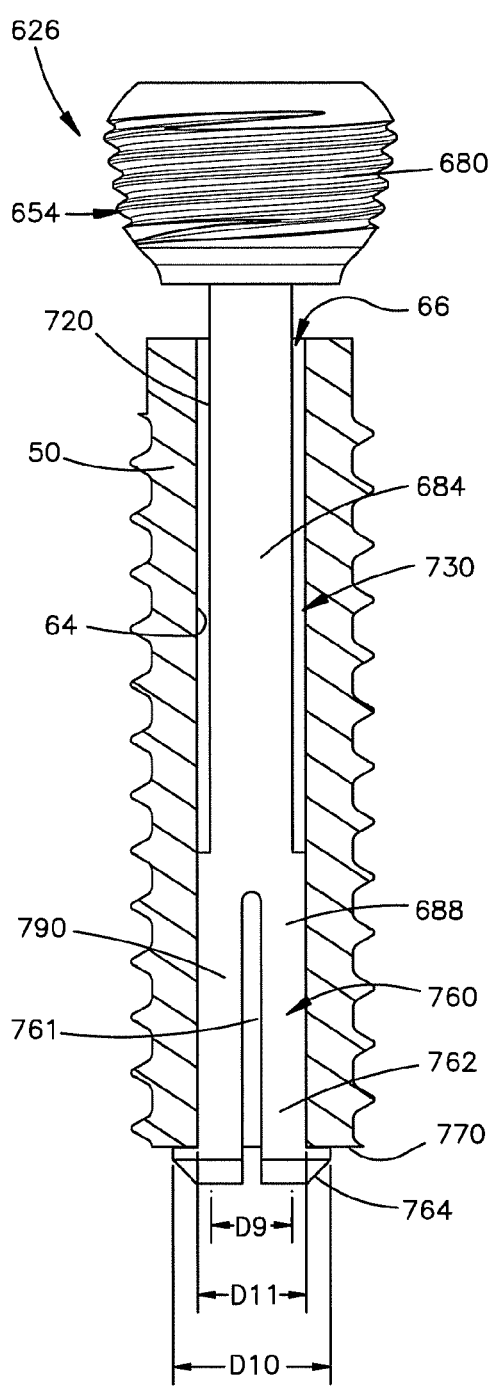
FIG. 7A is a cross-sectional view of a dynamic fixation element in accordance with another embodiment, the dynamic fixation element having a sleeve, and a fixation member that includes an abutment member that couples the fixation member to the sleeve such that the abutment member is fixed along a direction that is perpendicular to a direction in which the fixation member extends through the sleeve.

In another embodiment and in reference to FIG. 7A, a dynamic fixation element 626 can include a sleeve 50 and a fixation member 654 coupled to the sleeve such that a proximal end of the fixation member 654 is moveable relative to the sleeve 50 while a distal end is fixed. The fixation member 654 is identical to the fixation member 354 shown in FIGS. 5A-5D and includes like structure unless otherwise described. Moreover, the dynamic bone fixation element 626 operates and functions in a similar manner as the dynamic bone fixation element 326 unless otherwise described.

As shown in FIG. 7A, the fixation member 654 extends through the channel 66 of the sleeve 50 along the first direction $X_1$ and includes a head 680, a shaft 684 extending distally from the head 680 along a second direction $X_2$, and an abutment member 688 extending from the shaft 684. As shown, the abutment member 688 can extend from a distal end of the shaft 684 such that at least a portion of the abutment member 688 extends along a direction that is perpendicular to the second direction $X_2$ and the sleeve 50 is captured between the head 680 and the abutment member 688. In this way, the sleeve 50 is coupleable to the fixation member 654.

The shaft 684 extends distally from the head 680. The shaft 684 includes at least an outer surface 720 that faces the inner surface 64 of the channel 66. As shown in FIG. 7A, the outer surfaces 720 of the shaft 684 each face a respective inner surface 64 of the channel 66 such that respective non-zero gaps 730 are defined between the outer surfaces 720 and the inner surfaces 64. Therefore, at least a portion of the shaft 684 that is within the channel 66 has a cross-sectional dimension $D_9$ measured along a direction perpendicular to the second direction $X_2$ that is less than the cross-sectional dimension $D_1$ of the channel 66. Therefore the fixation member 654 is received by the channel 66 such that the head 680 is moveable relative to the sleeve 50 along at least a direction that has a directional component that is transverse to the first direction $X_1$. In particular, the head 680 is moveable relative to the sleeve 50 along a plurality of directions, each direction of the plurality of directions having a directional component that is transverse to the first direction $X_1$. It should be appreciated, however that the dimension $D_9$ can be the same for the entire length of the shaft 684 or the dimension $D_9$ can vary along the length of the shaft 684 so long as the head 680 is capable of moving relative to the sleeve 50 as described.

The abutment member 688 extends from a distal end of the shaft 684 and includes at least one such as four flexible extensions 760 that are separated from each other by elongate slots 761 and are configured to resiliently flex inward as the shaft 684 is passed through the channel 66 during assembly of the dynamic bone fixation element 626. Each flexible extension 760 includes an elongate body 762 and a shelf 764 that extends radially outward from a distal portion of the body 762 along a direction that is perpendicular to the second direction. The shelves 764 together define a shoulder 770 that has a cross-sectional dimension $D_{10}$ measured along a direction that is perpendicular to the second direction $X_2$ that is greater than the cross-sectional dimension $D_1$ of the channel 66. Therefore, the abutment member 688 is configured to limit movement of the fixation member 654 along the first direction relative to the sleeve 50.

With continued reference to FIG. 7A, a portion 790 of the abutment member 688 that is within the channel 66 has a cross-sectional dimension $D_{11}$ that is substantially equal to the cross-sectional dimension $D_1$ of the channel 66. Therefore, the abutment member 688 can be fixed relative to the sleeve 50 along a direction that is perpendicular to the first direction $X_1$. Thus it can be said that a distal end of the fixation member 654 can be fixed relative to the sleeve, while a proximal end of the fixation member 654 is moveable relative to the sleeve 50.

Figure 7B:
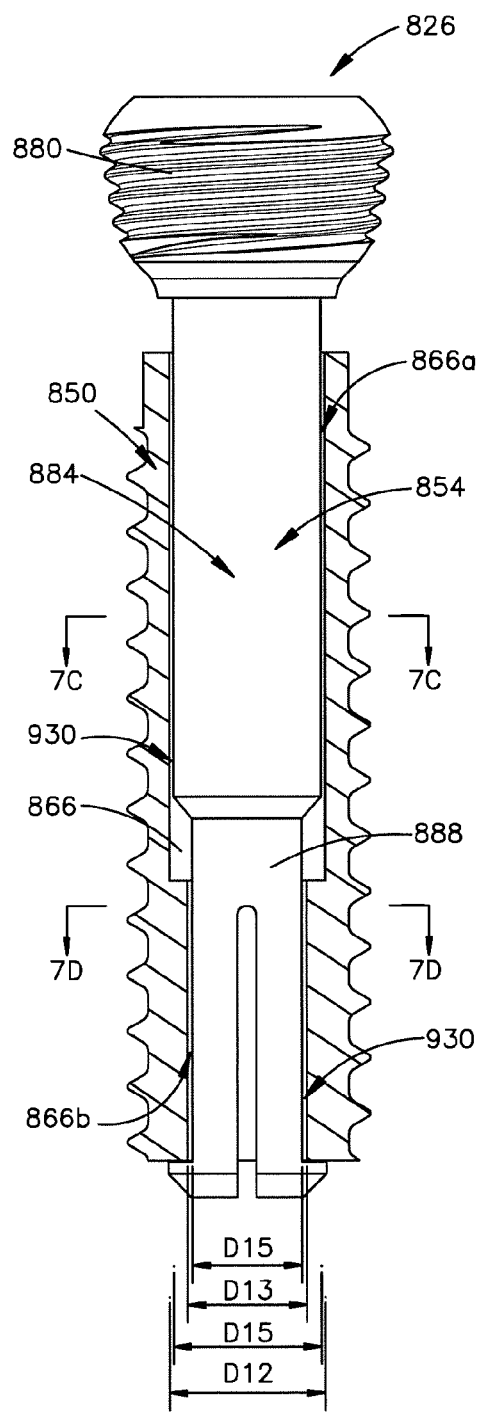
FIG. 7B is a cross-sectional view of a dynamic fixation element in accordance with another embodiment, the dynamic fixation element having a sleeve that defines a proximal channel portion and a distal channel portion, and a fixation member that includes a proximal shaft portion and a distal shaft portion, the proximal shaft portion being circular shaped in cross-section, and the distal shaft portion being polygonal shaped in cross-section.
Figure 7C:
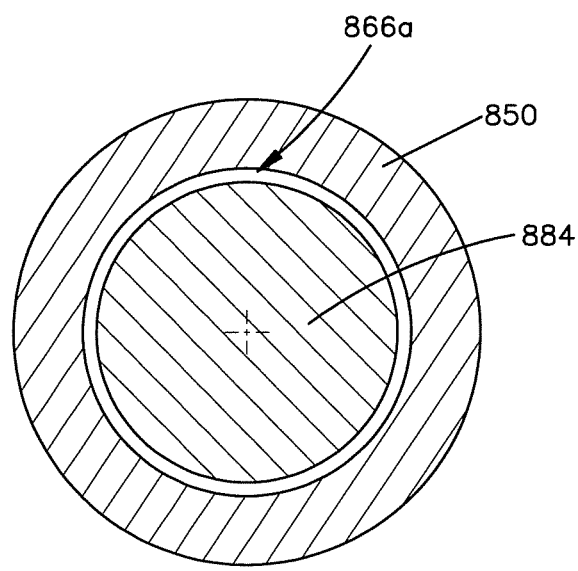
FIG. 7C is a cross-sectional view of the dynamic fixation element shown in FIG. 7B through the line 7C-7C.
Figure 7D:
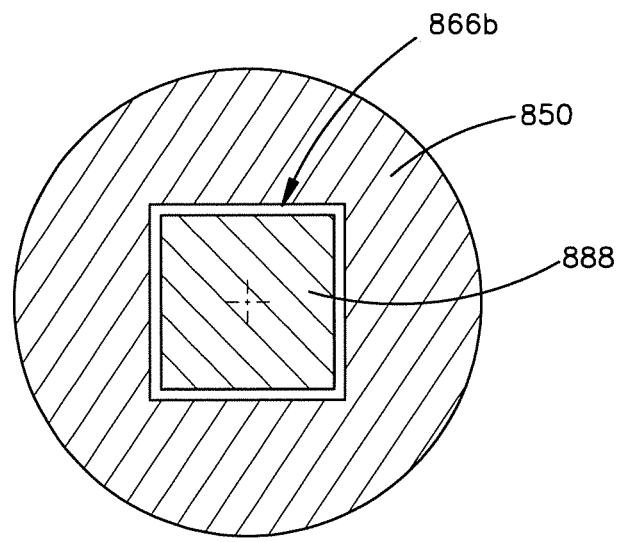
FIG. 7D is a cross-sectional view of the dynamic fixation element shown in FIG. 7B through the line 7D-7D.

Now in reference to FIGS. 7B-7D, and in accordance with another embodiment, a dynamic fixation element 826 can include a sleeve 850 and a fixation member 854 coupled to the sleeve 850 such that a portion of the fixation member 854 is cylindrical in cross-section and another portion is polygonal in cross-section. As shown in FIG. 7B, the fixation member 854 is coupled to the sleeve 850 in a similar manner as the fixation member 354 shown in FIGS. 5A-5D is coupled to the sleeve and includes like structure unless otherwise described.

As shown in FIG. 7B, the sleeve 850 defines a channel 866 that includes a proximal channel portion 866a and a distal channel portion 866b. The proximal channel portion 866a can define a cross-sectional dimension $D_{12}$ and the distal channel portion 866b can define a cross-sectional dimension $D_{13}$ that is less than that of the proximal channel portion 866b. As shown in FIGS. 7C and 7D, the proximal channel portion 866a can be circular shaped in cross-section and the distal channel portion 866b can be polygonal shaped (e.g. square shaped, hexagonal shaped, etc.) in cross-section. It should be appreciated, however, that the proximal channel portion 866a and the distal channel portion 866b can have any shape and dimensions as desired.

With continued reference to FIGS. 7B-7D, the fixation member 854 extends through the channel 866 of the sleeve 850 along the first direction $X_1$ and includes a head 880, a shaft 884 extending distally from the head 880 along a second direction $X_2$, and an abutment member 888 extending from the shaft 884. As shown, the abutment member 888 can extend from a distal end of the shaft 884 such that at least a portion of the abutment member 888 extends along a direction that is perpendicular to the second direction $X_2$ and the sleeve 850 is captured between the head 880 and the abutment member 888. In this way, the sleeve 850 is coupleable to the fixation member 854 or otherwise trapped by the fixation member 854.

As shown in FIG. 7B, the shaft 884 extends distally from the head 880 and the abutment member 888 extends distally from the shaft 884. As shown in FIG. 7B, the shaft 884 can define a cross-sectional dimension $D_{14}$ and the portion of the abutment member 888 that is within the channel 866 can define a cross-sectional dimension $D_{15}$ that is less than that of the shaft 884. As shown in FIGS. 7C and 7D, the shaft 884 can be circular shaped in cross-section and the portion of the abutment member 888 that is within the distal channel portion 866b can be polygonal shaped (e.g. square shaped, hexagonal shaped, etc.) in cross-section. Further, the dimension $D_{14}$ of the shaft 884 can be less than the dimension $D_{12}$ of the proximal channel portion 866a such that gaps 930 are formed between an outer surface of the shaft 884 and an inner surface of the sleeve 850 that defines the proximal channel portion 866a. Similarly, the dimension $D_{13}$ can be less than the dimension $D_{15}$ such that gaps 930 are formed between outer surfaces of the abutment member 888 and inner surfaces of the sleeve 850 that define the distal channel portion 866b. Therefore the fixation member 854 can be received by the channel 866 such that the head 880 is moveable relative to the sleeve 850 along all directions having a directional component that is transverse to the first direction $X_1$ and such that rotation of the fixation member 854 causes the sleeve 850 to rotate along with the fixation member 854.

Figures 8A, 8B:
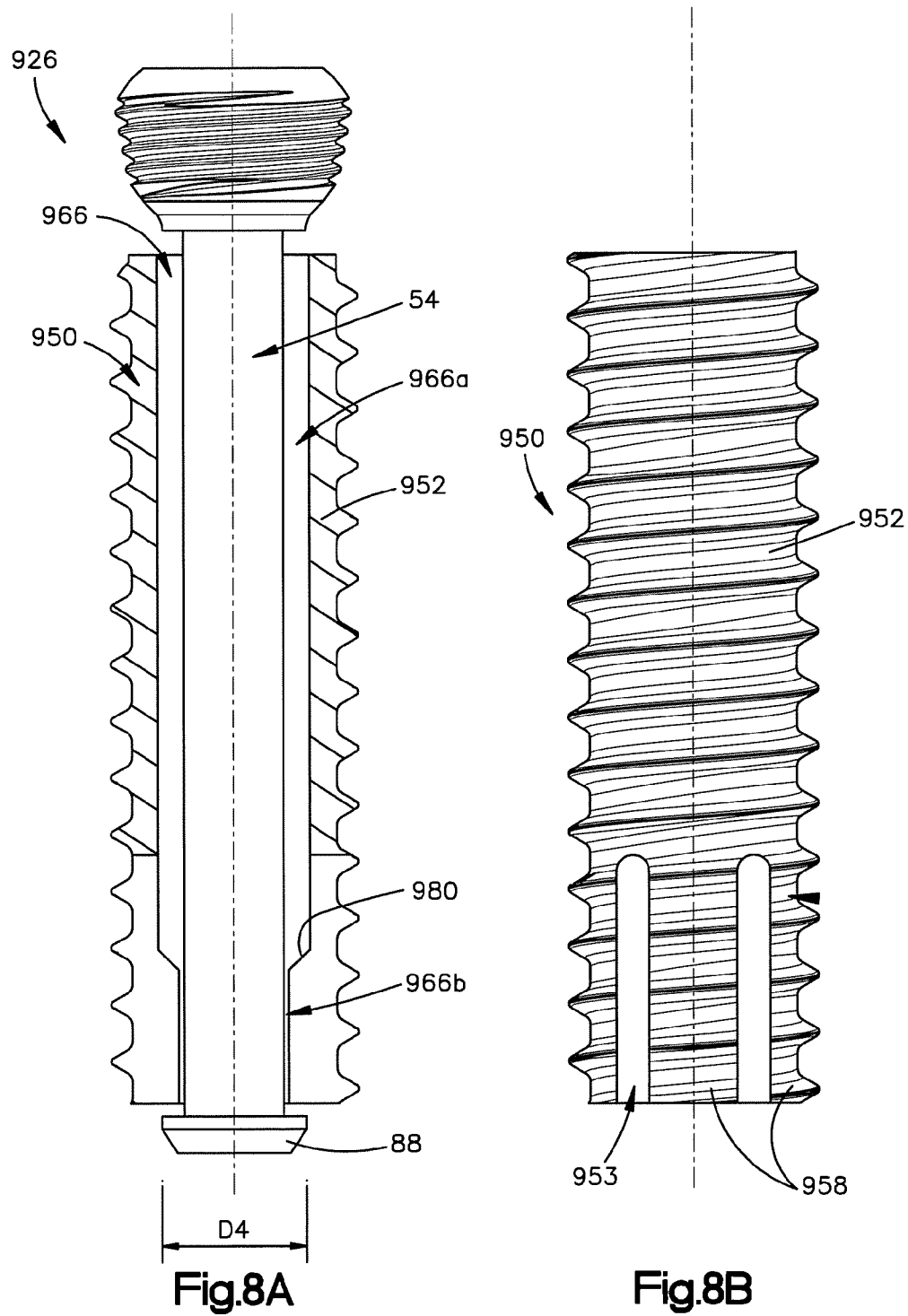
FIG. 8A is a side elevation view of a sleeve in accordance with another embodiment, the sleeve including a plurality of flexible legs at a distal end of the sleeve.
FIG. 8B is a cross-sectional view of a dynamic fixation element including the sleeve shown in FIG. 8A.

Now in reference to FIGS. 8A and 8B, a dynamic fixation element 926 can include a sleeve 950 that defines a plurality of flexible legs 958, and a fixation member such as fixation member 54 coupled to the sleeve 950. As shown in FIGS. 8A and 8B, the fixation member 54 can be identical to the fixation member shown in FIGS. 2A-2E, and the sleeve 950 can be configured such that as the fixation member passes through a channel 966 of the sleeve 950, the flexible legs 958 will flex outward to allow the abutment member to pass through a channel 966 of the sleeve 950. It should be appreciated, however, that the fixation member can have any configuration as desired. For example, the fixation member can be similar to the fixation member 354 shown in FIGS. 5A-5D.

As shown in FIGS. 8A and 8B, the sleeve 950 includes a body 952 that is elongate along the first direction and a channel 966 that extends through the body 952 along the first direction. A distal end of the body 952 includes a plurality of cutouts 953 that define the flexible legs 958. The flexible legs 958 are elastically flexible such that as the fixation member 954 is passed through the channel 966, the flexible legs 958 will flex outwardly until the abutment member 88 of the fixation member 54 has passed through the channel 966. As shown in FIG. 8A, the channel 966 can have a proximal channel portion 966a and a distal channel portion 966b. The proximal channel portion 966a can have a cross-sectional dimension that is greater than that of the distal channel portion 966b. For example, the proximal channel portion 966a can have a cross-sectional dimension that is equal to or greater than the cross-sectional dimension $D_4$ of the abutment member 88 so that the abutment member 88 can pass through the proximal channel portion 966a.

The cross-sectional dimension of the proximal portion 966b can be less than the cross-sectional dimension $D_4$ of the abutment member 88 such that as the abutment member 88 passes through the distal channel portion 966b, the abutment member 88 causes the flexible legs 958 to flex outward so as to allow the abutment member 88 to pass through the distal channel portion 966b.

With continued reference to FIG. 8A, the sleeve 950 can define a ramped portion 980 that transitions the proximal channel portion 966a to the distal channel portion 966b. As the fixation member 54 is passed through the channel 966, the abutment member 88 will ride against the ramped portion 980 to thereby cause the flexible legs 958 to flex outward. When the abutment member 88 has passed completely through the channel 966 the flexible legs 958 will return substantially to their initial position such that the sleeve 950 is trapped between the abutment member 88 and the head 80 of the fixation member 54.

Figure 9C:
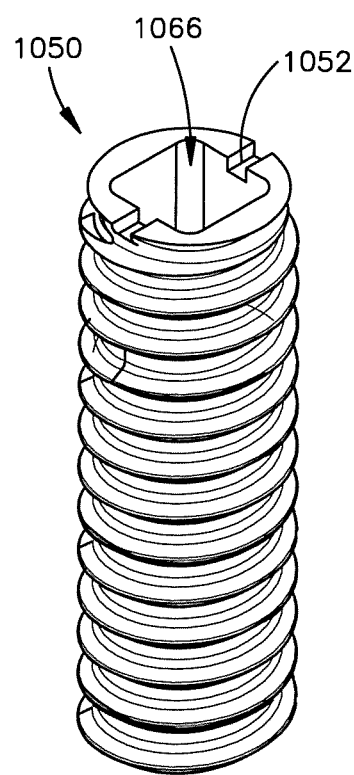
FIG. 9C is a side perspective view of a sleeve having a mating feature configured to receive a mating end of a screw driver.

Now in reference to FIGS. 9A-9E, a bone fixation system 1010 can include a load carrier configured as a bone plate 1022, fixation members 1054 that are pre-assembled or otherwise pre-coupled to the bone plate 1022 so as to form an implant 1024, and corresponding sleeves 1050 that can receive respective fixation members 1054. The fixation members 1054 can be pre-coupled to the bone plate 1022 by inserting the fixation members 1054 through respective holes of the plate 1022 to thereby form the implant 1024, as shown in FIG. 9A, or the bone plate 1022 and the fixation members 1054 can be pre-coupled such that the bone plate 1022 and the fixation members 1054 are integrally formed so as to form a monolithic implant 1054 as shown in FIG. 9B.

Figure 9D:
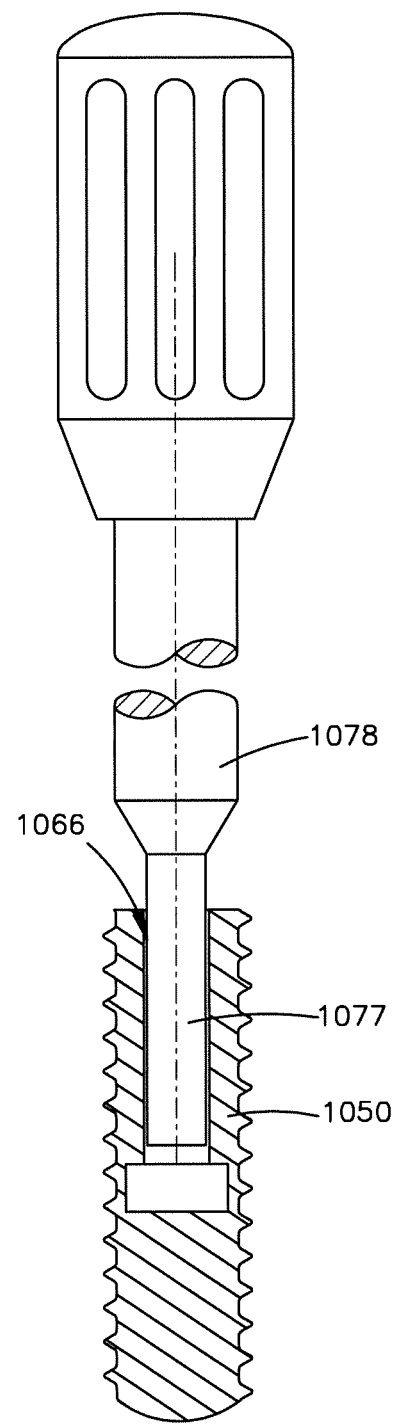
FIG. 9D is a side perspective view of a sleeve having a mating feature defined by the channel such that the channel is configured to receive the mating end of the screw driver.

As shown in FIG. 9C, the sleeves 1050 can include a mating feature 1052 at its proximal end. Otherwise the sleeve 1050 is constructed in accordance with any of the previously described sleeves. The mating feature 1052 can be a slot that is configured to receive a screw driver such that rotation of the screw driver will drive the sleeve 1050 into the anatomical structure. It should be appreciated, however, that the sleeves 1050 can each define a channel 1066 that is shaped to receive a driver mating interface 1077 of a driver 1078 such that rotation of the driver 1078 will cause the sleeve 1050 to rotate as shown in FIG. 9D. For example, both the channel 1066 and the mating interface 1077 of the driver can be polygonal shaped in cross-section, such as square or hexagonal shaped.

In operation a drill guide can be placed against the anatomical structures that are to be joined by the bone plate 1022 so that holes can be formed in the anatomical structures. Once formed, the sleeves 1050 can be driven or otherwise placed in the drilled holes. The pre-assembled or otherwise pre-coupled implant can then be coupled to the sleeves 1050. That is the fixation members 1054 that are pre-coupled to the bone plate 1020 can be snapped into or otherwise mated with the sleeves 1050 as shown in FIG. 9E.

Figure 10:
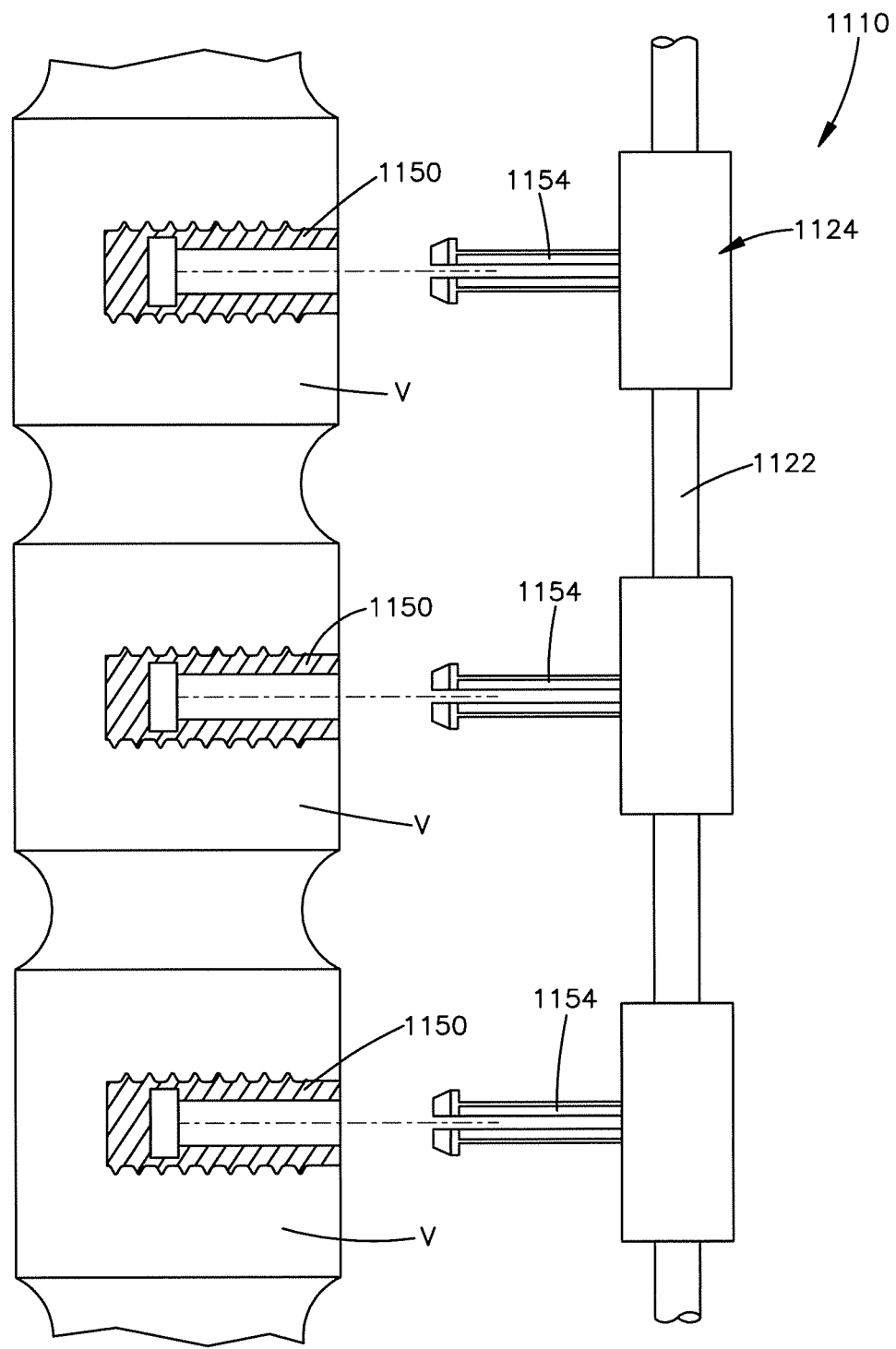
FIG. 10 is a side perspective view of an implant in accordance with another embodiment, the implant being coupled to sleeves that have been driven into respective vertebral bodies.

Now in reference to FIG. 10, a bone fixation system 1110 can be configured as a spinal fixation system and can include a load carrier that is configured as a spinal rod 1122 that can be coupled to a plurality of vertebral bodies V, such as to respective pedicles of the vertebral bodies, or to any other portions of the vertebral bodies as desired. The system 1110 can further include a plurality of fixation members 1154 that are pre-assembled or otherwise pre-coupled to the spinal rod 1122 so as to form an implant 1124, and corresponding sleeves 1150 that can receive respective fixation members 1154. The fixation members 1154 can be pre-coupled to the spinal rod 1122 by manually assembling the fixation members 1154 to the spinal rod 1122, or the spinal rod 1122 and fixation members 1154 can be pre-coupled such that the spinal rod 1122 and fixation members 1154 are integrally formed so as to form a monolithic implant 1124. It should be appreciated that the features of the fixation system 1110 can be incorporated into any spinal fixation system, as desired. For example, the features of the fixation system 1110 can be incorporated in the spinal fixation systems shown in United States Publication No. 2011/0106166, the contents of which are hereby incorporated by reference herein.

In operation a drill guide can be placed against the vertebral bodies V that are to be joined by the spinal rod 1122 so that holes can be formed in the vertebral bodies. Once formed, the sleeves 1150 can be driven or otherwise placed in the drilled holes. The pre-assembled or otherwise pre-coupled implant can then be coupled to the sleeves 1150. That is the fixation members 1154 that are pre-coupled to the spinal rod 1120 can be snapped into or otherwise mated with the sleeves 1150 as shown in FIG. 10.

The fixation elements can be configured to have a variety of lengths and thus can be configured to have variable gaps between the head and the sleeve that vary from a variety of maximum gaps. For example, fixation elements as described herein that are configured to be attached to a skull or the cranial maxilla facial area can be constructed such that the maximum gaps range between about 0.15 mm and about 0.4 mm. That is, a fixation element having an overall length of 1 mm can have a channel length of about 0.5 mm, a shaft length of about 0.35 mm, and a maximum gap of 0.15 mm between the head and the sleeve, a fixation element having an overall length of 2.7 mm can have a channel length of about 2.0 mm, a shaft length of about 1.6 mm, and a maximum gap of 0.2 mm between the head and the sleeve, and a fixation element having an overall length of about 5.0 mm can have a channel length of about 3.2 mm, a shaft length of about 2.6 mm, and a maximum gap of 0.4 mm between the head and the sleeve. Therefore it can be said that the fixation element can have an overall length that is less than 5.0 mm. It should be appreciated, however, that the listed dimensions are for example only, and the fixation elements described can have any dimensions as desired.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. For example, dynamic bone fixation element 26 can be constructed such that the gap 480 is defined between at least one of the sleeve 50 and the head 80 or the sleeve 50 and the abutment member 88 or any of the channels of the sleeves can by completely cylindrical. It should be further appreciated that the dynamic bone fixation elements 26 and 326 can be manufactured using any technique as desired, and is not limited to those described herein. It is understood, therefore, that this invention is not limited to the particular embodiments disclosed, but it is intended to cover modifications within the spirit and scope of the present disclosure.

What is claimed:

1. A dynamic bone fixation element configured to couple a load carrier to bone, the dynamic bone fixation element comprising:
    a sleeve that is elongate along a first direction, the sleeve defining a proximal end, a distal end spaced from the proximal end along the first direction, and a channel that extends through the proximal end and toward the distal end along the first direction, the channel having a first cross-sectional dimension measured along a direction that is perpendicular to the first direction, the sleeve further defining an outer surface that is configured to engage bone; and
    a fixation member having a head, a shaft that extends from the head along a second direction, and an abutment member that extends from the shaft such that at least a portion of the abutment member faces the head, wherein the shaft is configured to extend into the channel such that at least a portion of the sleeve is captured between the abutment member and the head to thereby couple the fixation member to the sleeve,
    wherein at least a portion of the shaft that is configured to be within the channel has a second cross-sectional dimension along a direction perpendicular to the second direction, the second cross-sectional dimension being less than the first cross-sectional dimension such that the fixation member is moveable with respect to the sleeve along a direction that has a directional component transverse to the first direction, and
    wherein the abutment member extends from the distal end of the shaft in a third direction that is perpendicular to the second direction, the shaft has an outer perimeter that extends from the head to the abutment member, and the shaft is solid around the outer perimeter.

2. The dynamic fixation element according to claim 1, wherein a gap is defined between at least one of (i) the sleeve and the head and (ii) the sleeve and the abutment member, when the fixation member is coupled to the sleeve.

3. The dynamic fixation element according to claim 1, wherein the fixation member is configured to extend through the channel such that the second direction is parallel to the first direction.

4. The dynamic bone fixation element according to claim 1, wherein the head defines a shoulder and the entire sleeve is configured to be captured between the abutment member and the shoulder such that the fixation member is moveable relative to the sleeve along the first direction.

5. The dynamic bone fixation element according to claim 1, wherein the head defines a shoulder and the entire sleeve is configured to be captured between the abutment member and the shoulder such that the fixation member is only moveable relative to the sleeve along the transverse direction.

6. The dynamic bone fixation element of claim 1, wherein the fixation member is moveable relative to the sleeve along a plurality of directions when the fixation member is coupled to the sleeve, each direction of the plurality of directions having a directional component that is transverse to the first direction.

7. The dynamic bone fixation element according to claim 1, wherein a cross-section of the channel is non-circular and a cross-section of the shaft is non-circular such that rotation of the fixation member causes the sleeve to rotate when the fixation member is coupled to the sleeve.

8. The dynamic bone fixation element of claim 7, wherein the cross-section of the channel is polygonal shaped and the cross-section of the shaft is polygonal shaped.

9. The dynamic bone fixation element according to claim 1, wherein the abutment member has a third cross-sectional dimension that is greater than the first cross-sectional dimension.

10. The dynamic bone fixation element according to claim 1, wherein the head includes an external thread that is configured to engage an internal thread of a bone plate.

11. The dynamic bone fixation element according to claim 1, wherein the fixation member has an overall length that is less than 5.0 mm.

12. The dynamic bone fixation element according to claim 1, wherein the fixation member is made of a first material, and the sleeve is made from a second material, the first material being stiffer than the second material.

13. The dynamic bone fixation element of claim 12, wherein the first material comprises Cobalt Chromium and the second material comprises Titanium.

14. The dynamic bone fixation element according to claim 1, wherein the outer surface of the sleeve carries a thread that is configured to engage bone.

15. The dynamic bone fixation element according to claim 1, wherein a distal end of the fixation member is moveable with respect to the sleeve when the fixation member is coupled to the sleeve.

16. The dynamic bone fixation element according to claim 1, wherein the sleeve defines a plurality of flexible legs that are configured to flex outwardly as the abutment member passes through the channel.

17. The dynamic bone fixation element according to claim 1, wherein the channel includes a proximal portion and a distal portion, the proximal portion being circular in cross-section and the distal portion being polygonal in cross-section.

18. A dynamic bone fixation element configured to couple a load carrier to bone, the dynamic bone fixation element comprising:
    a sleeve that is elongate along a first direction, the sleeve defining a proximal end, a distal end spaced from the proximal end along the first direction, and an inner surface that at least partially defines a channel, the channel extending along the first direction through the proximal end and toward the distal end, the sleeve further defining an outer surface that is configured to engage bone; and
    a fixation member coupled to the sleeve, the fixation member having a head, a shaft extending from the head and into the channel, and an abutment member extending from the shaft such that at least a portion of the sleeve is captured between the head and the abutment member, wherein the fixation member is movable with respect to the sleeve along the first direction and along a second direction that has a directional component that is transverse to the first direction, and wherein at least the abutment member defines an abutment surface that is sized to contact the sleeve so as to limit translation of the fixation member relative to the sleeve along the first direction, and
    wherein the abutment member has a cross-sectional dimension in the second direction that is greater than that of the channel, and the abutment member further has an outer perimeter that is in plane with the cross-sectional dimension and that extends continuously around the abutment member.

19. The dynamic bone fixation element according to claim 18, wherein the shaft includes a surface that faces and is spaced apart from the inner surface of the sleeve such that the fixation member can move relative to the sleeve along the second direction.

20. The dynamic bone fixation element according to claim 18, wherein the head defines a respective abutment surface that is sized to contact the sleeve so as to limit translation of the fixation member relative to the sleeve along the first direction.

21. The dynamic bone fixation element of claim 20, wherein the cross-section of the channel is polygonal shaped and the cross-section of the shaft is polygonal shaped.

22. The dynamic bone fixation element according to claim 20, wherein the abutment surface of the head is configured to abut the proximal end of the sleeve and the abutment surface of the abutment member is configured to abut the distal end of the sleeve.

23. The dynamic bone fixation element of claim 22, wherein the abutment surface of the head is spaced from the abutment surface of the abutment member by a first length, and the distal end of the sleeve is spaced from the proximal end of the sleeve by a second length, the first length being greater than the second length.

24. The dynamic bone fixation element according to claim 18, wherein a cross-section of the channel is non-circular and a cross-section of the shaft is non-circular such that rotation of the fixation member causes the sleeve to rotate.

25. The dynamic bone fixation element according to claim 18, wherein the abutment member has a cross-sectional dimension that is greater than that of the channel.

26. The dynamic bone fixation element according to claim 18, wherein the head includes an external thread that is configured to engage an internal thread of a bone plate.

27. The dynamic bone fixation element according to claim 18, wherein the fixation element has an overall length that is less than 5 mm.

28. The dynamic bone fixation element according to claim 18, wherein the fixation member is made of a first material, and the sleeve is made from a second material, the first material is stiffer than the second material.

29. The dynamic bone fixation element of claim 28, wherein the first material comprises Cobalt and the second material comprises Titanium.

30. The dynamic bone fixation element according to claim 18, wherein the outer surface of the sleeve carries a thread that is configured to engage bone.

31. The dynamic bone fixation element according to claim 18, wherein the sleeve defines a plurality of flexible legs that are configured to flex outwardly as the abutment member passes through the channel.

32. The dynamic bone fixation element according to claim 18, wherein the channel includes a proximal portion and a distal portion, the proximal portion being circular in cross-section and the distal portion being polygonal in cross-section.

33. A dynamic bone fixation element configured to couple a load carrier to bone, the dynamic bone fixation element comprising:
a sleeve that is elongate along a first direction, the sleeve defining a proximal end, a distal end spaced from the proximal end along the first direction, and an inner surface that at least partially defines a channel, the channel extending through the proximal end, and further extending from the proximal end along the first direction toward the distal end, the sleeve further defining an outer surface that is configured to engage bone; and
a fixation member having a head, a shaft extending from the head and into the channel, and an abutment member having at least a portion that protrudes radially outward relative to the shaft along a second direction that is substantially perpendicular to the first direction, wherein the abutment member at least partially couples the fixation member to the sleeve such that both the abutment member and the head are moveable with respect to the sleeve along a third direction that has a directional component perpendicular to the first direction, and wherein the abutment member has a cross-sectional dimension in the second direction that is greater than that of the channel and the abutment member is solid along the cross-sectional dimension.

34. The dynamic bone fixation element according to claim 33, wherein the entire sleeve is captured between the head and the abutment member.

35. The dynamic bone fixation element according to claim 33, wherein the shaft has a surface that is spaced apart from the inner surface.

36. The dynamic bone fixation element according to claim 33, wherein the head defines a first abutment surface that is configured to abut the proximal end of the sleeve and the abutment member defines a second abutment surface that is configured to abut the distal end of the sleeve.

37. The dynamic bone fixation element of claim 33, wherein the first abutment surface is spaced from the second abutment surface by a first length, and the distal end of the sleeve is spaced from the proximal end of the sleeve by a second length, the first length being greater than the second length.

38. The dynamic bone fixation element according to claim 33, wherein a cross-section of the channel is polygonal shaped and a cross-section of the shaft is polygonal shaped such that rotation of the shaft causes the sleeve to rotate.

39. The dynamic bone fixation element according to claim 33, wherein the abutment member has a cross-sectional dimension that is greater than that of the channel.

40. The dynamic bone fixation element of claim 33, wherein the channel includes a first portion and a second portion that is distal to the first portion, the second portion having a cross-sectional dimension that is greater than that of the first portion.

41. The dynamic bone fixation element according to claim 33, wherein the outer surface of the sleeve carries a thread that is configured to engage bone.

* * * * *